United States Patent
Cho et al.

(10) Patent No.: US 8,754,210 B2
(45) Date of Patent: Jun. 17, 2014

(54) METHOD FOR PREPARING 5-CHLORO-N-({(5S)-2-OXO-3-[4-(5,6-DIHYDRO-4H-[1,2,4]TRIAZIN-1-YL)PHENYL]-1,3-OXAZOLIDIN-5-YL}METHYL) DERIVATIVE AND INTERMEDIATE USED THEREIN

(75) Inventors: Young Lag Cho, Daejeon (KR); Sang Eun Chae, Daejeon (KR); Seong Jin Kim, Daejeon (KR); Ho Young Song, Daejeon (KR); Tae Kyo Park, Daejeon (KR); Sung Ho Woo, Daejeon (KR); Yong Zu Kim, Daejeon (KR); Jinhwa Lee, Yongin-si (KR); Suk Ho Lee, Yongin-si (KR)

(73) Assignees: Green Cross Corporation, Yongin-si (KR); Legochem Bioscience Ltd., Daejeon (KR)

( * ) Notice: Subject to any disclaimer, the term of this patent is extended or adjusted under 35 U.S.C. 154(b) by 197 days.

(21) Appl. No.: 13/382,235

(22) PCT Filed: Jul. 7, 2010

(86) PCT No.: PCT/KR2010/004421
§ 371 (c)(1),
(2), (4) Date: Jan. 4, 2012

(87) PCT Pub. No.: WO2011/005029
PCT Pub. Date: Jan. 13, 2011

(65) Prior Publication Data
US 2012/0136149 A1    May 31, 2012

(30) Foreign Application Priority Data

Jul. 8, 2009   (KR) .................. 10-2009-0062090

(51) Int. Cl.
C07D 413/10    (2006.01)
C07D 413/14    (2006.01)
C07D 253/065   (2006.01)
C07D 409/10    (2006.01)

(52) U.S. Cl.
USPC ............................. 544/182; 549/69

(58) Field of Classification Search
USPC ............................................. 544/182
See application file for complete search history.

(56) References Cited

U.S. PATENT DOCUMENTS 8,178,525 B2 *   5/2012   Song et al. ............... 514/229.2
2003/0153610 A1  8/2003   Straub et al.

FOREIGN PATENT DOCUMENTS

KR   10-0804932 B1   2/2008
KR   10-0898361 B1   5/2009

OTHER PUBLICATIONS

Schulz et al., Chemische Berichte, 122(10), 1983-7, 1989 (CAPLUS abstract provided).*
Minlibaeva et al. Org. Khim., 99-102, 1976 (CAPLUS abstract provided).*
Deng Hong, et al., "Copper-Catalyzed Tandem Nucleophilic Ring-Opening/Intramolecular Oxidative Amidation og N-Tosylaziridines and Hydrazones under Aerobic Conditions", Organic Letters, 2009, pp. 5678-5681, vol. 11, No. 24.

* cited by examiner

Primary Examiner — Venkataraman Balasubramanian
(74) Attorney, Agent, or Firm — Sughrue Mion, PLLC

(57) ABSTRACT

Disclosed are: a method for preparing a 5-chloro-N-({(5S)-2-oxo-3-[4-(5,6-dihydro-4H-[1,2,4]triazin-1-yl)phenyl]-1,3-oxazolidin-5-yl}-methyl)thiophene-2-carboxamide derivative, which is a inhibitor of blood coagulation factor Xa, in a high purity and yield; and a novel intermedicate used therein.

6 Claims, No Drawings

METHOD FOR PREPARING 5-CHLORO-N-({(5S)-2-OXO-3-[4-(5,6-DIHYDRO-4H-[1,2,4]TRIAZIN-1-YL)PHENYL]-1,3-OXAZOLIDIN-5-YL}METHYL) DERIVATIVE AND INTERMEDIATE USED THEREIN

CROSS REFERENCE TO RELATED APPLICATIONS

This application is a National Stage of International Application No. PCT/KR2010/004421 filed Jul. 7, 2010, claiming priority based on Korean Patent Application No. 10-2009-0062090 filed Jul. 8, 2009 the contents of all of which are incorporated herein by reference in their entirety.

FIELD OF THE INVENTION

The present invention relates to a novel method for preparing a 5-chloro-N-({(5S)-2-oxo-3-[4-(5,6-dihydro-4H-[1,2,4]triazin-1-yl)phenyl]-1,3-oxazolidin-5-yl}-methyl) thiophene-2-carboxamide derivative which is an inhibitor of blood coagulation factor Xa, and a novel intermediate used in preparing the same.

BACKGROUND OF THE INVENTION

5-Chloro-N-({(5S)-2-oxo-3-[4-(5,6-dihydro-4H-[1,2,4]triazin-1-yl)phenyl]-1,3-oxazolidin-5-yl}-methyl) thiophene-2-carboxamide of formula (A) has been known as an inhibitor of blood coagulation factor Xa and used for treating and preventing thrombosis, myocardial infarction, arteriosclerosis, inflammation, stroke, angina pectoris, recurrent stricture after angioplasty, and thromboembolism such as intermittent claudication.

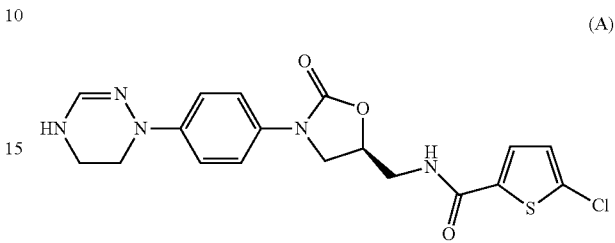

(A)

Korea Patent No. 2008-64178, whose application has been filed by the present invetors, discloses a use of the compound as an inhibitor of blood coagulation factor Xa and a preparation method thereof. The preparation method comprises the step of preparing a cyclic amidrazone starting from 4-nitroaniline, as shown in reaction scheme 1:

Reaction Scheme 1

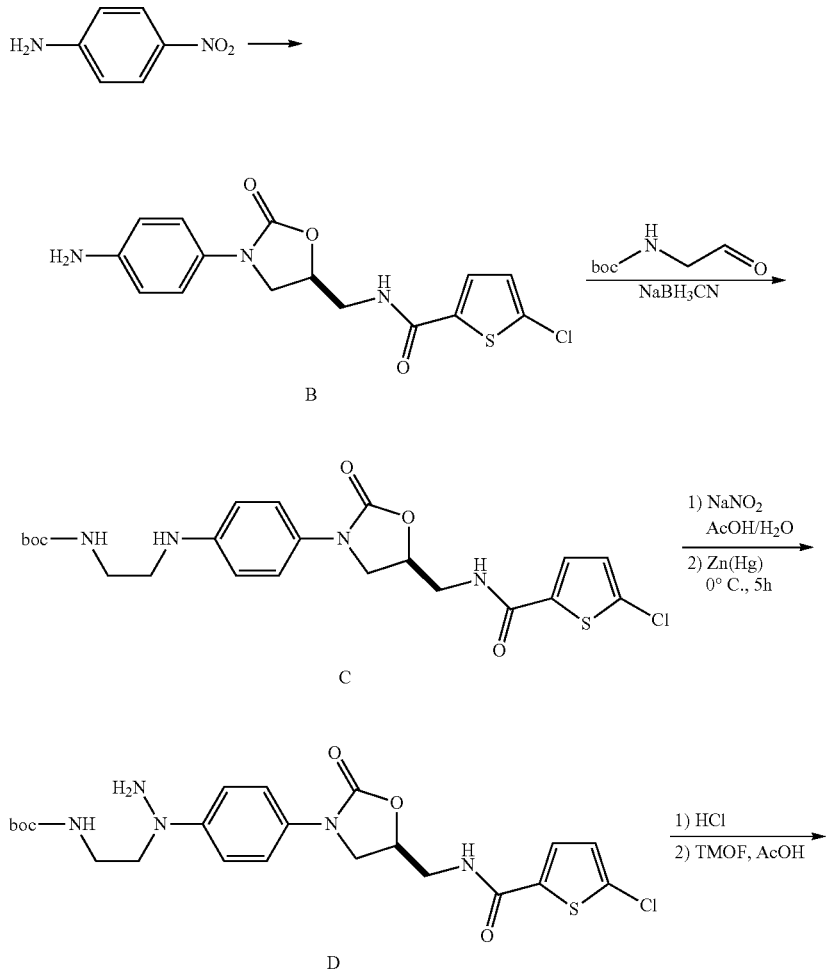

-continued

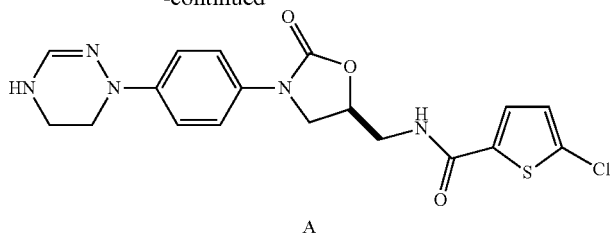

A

Specifically, the cyclic amidrazone (A) is prepared by the steps of: preparing the compound (B) using 4-nitroaniline; treating the compound (B) with a t-butoxycarbonyl amine protecting group to prepare the compound (C); introducing a nitroso group into the compound (C) using NaNO$_2$, followed by reduction using zinc to prepare the compound (D); and treating the compound (D) successively with hydrochloric acid and an ortho-formate.

However, the above preparation method is complicated and gives a low yield of the compound (A) (e.g., a total yield of 9%), and it also requires the use of a column chromatography purification step, which limits mass production of the cyclic amidrazone. In particular, the step for preparing the compound (D) from the compound (C) is required to use a harmful heavy metal-containg materal such as zinc amalgam which gives an unsatisfactorily low yield, and the isolation step of the compound (D) does not proceed easily.

SUMMARY OF THE INVENTION

It is a primary object of the present invention to provide a novel, simple method for preparing a high-purity 5-chloro-N-({(5S)-2-oxo-3-[4-(5,6-dihydro-4H-[1,2,4]triazin-1-yl)phenyl]-1,3-oxazolidin-5-yl}-methyl)thiophene-2-carboxamide economically in a high yield.

It is another object of the present invention to provide an intermediate used for preparing a 5-chloro-N-({(5S)-2-oxo-3-[4-(5,6-dihydro-4H-[1,2,4]triazin-1-yl)phenyl]-1,3-oxazolidin-5-yl}-methyl)thiophene-2-carboxamide, and a preparing method thereof.

In accordance with an aspect of the present invention, there is provided a method for preparing an oxazolidinone derivative of formula (I) or a pharmaceutically acceptable salt thereof, comprising the steps of:

introducing an amino protecting group to a cyclic amidrazone of formula (V) to obtain a compound of formula (VI);

reducing the nitro group of the compound of formula (VI) to obtain a compound of formula (VII);

subjecting the compound of formula (VII) to a reaction with 5-chloro-N-(((S)-oxiran-2-yl)methyl)thiophene-2-carboxamide to obtain a compound of formula (VIII) having a chlorothiophene group;

conducting a carbonylation reaction of the compound of formula (VIII) using a phosgene equivalent to obtain an oxazolidinone of formula (IX); and removing the amino protecting group from the amidrazone ring of the oxazolidinone of formula (IX),

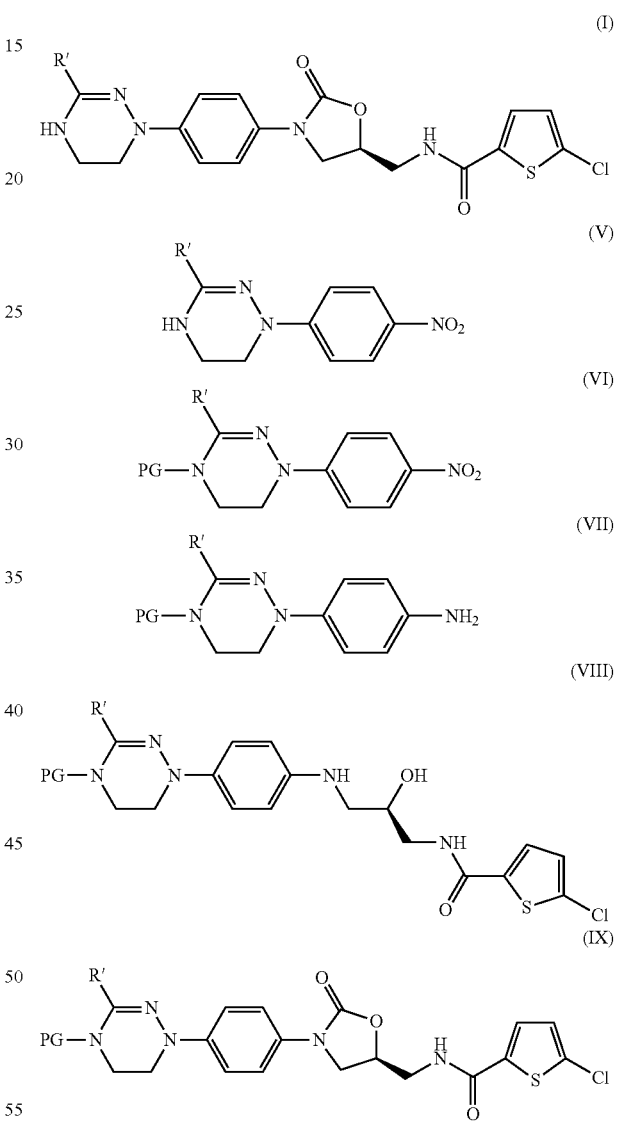

wherein,

R' is hydrogen, $C_1$-$C_7$ alkyl, $C_3$-$C_7$ cycloalkyl, $C_6$-$C_{12}$ aryl, or $C_4$-$C_{12}$ heteroaryl comprising 1 to 4 hetero atoms selected from the group consisting of oxygen, sulfur, and nitrogen; in which R' may be optionally substituted with one or more substituents selected from the group consisting of $C_1$-$C_7$ alkyl, $C_1$-$C_7$ haloalkyl, $C_1$-$C_7$ alkoxy, and halogen; and PG is formyl, ($C_1$-$C_7$ alkyl)carbonyl, ($C_1$-$C_7$ haloalkyl)carbonyl, ($C_6$-$C_{12}$ aryl)carbonyl, ($C_1$-$C_7$ alkoxy)carbonyl, ($C_6$-$C_{12}$ aryl)($C_1$-$C_7$ alkoxy)carbonyl, or trityl.

In accordance with another aspect of the present invention, there is provided a cyclic amidrazone of formula (V):

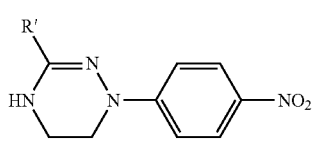

(V)

wherein,

R' is hydrogen, $C_1$-$C_7$ alkyl, $C_3$-$C_7$ cycloalkyl, $C_6$-$C_{12}$ aryl, or $C_4$-$C_{12}$ heteroaryl comprising 1 to 4 hetero atoms selected from the group consisting of oxygen, sulfur, and nitrogen; in which R' may be optionally substituted with one or more substitutents selected from the group consisting of $C_1$-$C_7$ alkyl, $C_1$-$C_7$ haloalkyl, $C_1$-$C_7$ alkoxy, and halogen.

DETAILED DESCRIPTION OF THE INVENTION

Hereinafter, a detailed description of the present invention is given.

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl, and hexyl.

As used herein, the term "cycloalkyl" refers to a saturated or partially unsaturated mono-, bi- or tri-cyclic hydrocarbon ring having 3 to 7 carbon atoms. Examples of "cycloalkyl" as used herein include, but are not limited to, cyclopropyl, cyclobutyl, cyclopentyl, cyclohexyl, and cycloheptyl.

As used herein, the term "aryl" refers to an optionally substituted mono-, bi-, tricyclic aromatic ring system. Exemplary optional substituents include substituted $C_1$-$C_3$ alkyl, substituted $C_2$-$C_3$ alkenyl, substituted $C_2$-$C_3$ alkynyl, heteroaryl, heterocyclic, aryl, alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamino, aminocarbonyl, carboxy, oxo, hydroxy, mercapto, amino, nitro, cyano, halogen, and ureido. Such a ring or ring system may be optionally fused to an aryl ring (e.g., benzene ring) optionally having one or more substituents, carbocycle ring, or a heterocyclic ring. Examples of "aryl" include, but are not limited to, phenyl, naphthyl, tetrahydronaphthyl, biphenyl, indanyl, anthracyl, and phenanthryl, as well as a substituted derivative thereof.

As used herein, the term "heteroaryl" refers to an optionally substituted monocyclic five- to six-membered aromatic ring containing one or more heteroatomic substitutions selected from S, SO, $SO_2$, O, N, and N-oxide; or refers to such an aromatic ring fused to one or more rings such as heteroaryl rings, aryl rings, heterocyclic rings, and carbocyclic rings (e.g., a bicyclic or tricyclic ring system), each having optional subsituents.

Examples of optional substituents are selected from the group consisting of substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamino, aminocarbonyl, carboxy, oxo, hydroxy, mercapto, amino, nitro, cyano, halogen, and ureido. Examples of "heteroaryl" used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted derivatives thereof.

As used herein, the term "halo" or "halogen" refers to fluorine (F), chlorine (Cl), bromine (Br), or iodine (I).

As used herein, the term "alkoxy" refers to the group —$OR_a$, wherein $R_a$ is alkyl, as defined above. Exemplary alkoxy groups useful in the present invention include, but are not limited to, methoxy, difluoromethoxy, trifluoromethoxy, ethoxy, n-propoxy, isopropoxy, n-butoxy, and t-butoxy.

As used herein, the term "alkylcarbonyl" refers to the group —(C=O)$R_a$, wherein $R_a$ is alkyl, as defined above. Exemplary alkylcarbonyl groups useful in the present invention include, but are not limited to, methylcarbonyl, ethylcarbonyl, n-propylcarbonyl, isopropylcarbonyl, n-butylcarbonyl group, and iso-butylcarbonyl group.

As used herein, the term "haloalkylcarbonyl" refers to the group —(C=O)$R_b$, wherein $R_b$ is alkyl substituted with one or more halogens, and the alkyl has the same meaning as defined above. Examples of the haloalkylcarbonyl group useful in the present invention include, but are not limited to, chloroacetyl, trifluoroacetyl, and pentafluoropropionyl.

As used herein, the term "arylcarbonyl" refers to the group —(C=O)$R_c$, wherein $R_c$ is aryl, as defined above. Exemplary arylcarbonyl groups useful in the present invention include, but are not limited to, phenylcarbonyl, naphthylcarbonyl, and indanylcarbonyl.

As used herein, the term "alkoxycarbonyl" refers to the group —(C=O)$R_d$, wherein $R_d$ is alkoxy, as defined above. Exemplary alkoxycarbonyl groups useful in the present invention include, but are not limited to, methoxycarbonyl, ethoxycarbonyl, and propoxycarbonyl.

As used herein, the term "arylalkoxycarbonyl" refers to the group —(C=O)$R_e$, wherein $R_e$ is an alkoxy group substituted with aryl, alkoxy and aryl having the same meanings as defined above. Exemplary arylalkoxycarbonyl groups useful in the present invention include, but are not limited to, benzyloxycarbonyl, 2-phenylethoxycarbonyl, 3-phenylpropoxycarbonyl, and the like. The preferred arylalkoxycarbonyl group is benzyloxycarbonyl.

As used herein, the term "alkylsulfonyloxy" refers to the group —O($SO_2$)$R_a$, wherein $R_a$ is alkyl, as defined above. Exemplary alkylsulfonyloxy groups useful in the present invention include, but are not limited to, methylsulfonyloxy, ethylsulfonyloxy, propylsulfonyloxy, and butylsulfonyloxy group.

As used herein, the term "arylsulfonyloxy" refers to the group —O($SO_2$)$R_c$, wherein $R_c$ is aryl, as defined above. Exemplary arylsulfonyloxy groups useful in the present invention include, but are not limited to, phenylsulfonyloxy, α-naphthylsulfonyloxy, β-naphthylsulfonyloxy, p-methylphenylsulfonyloxy, 4-tert-butylphenylsulfonyloxy, and 6-ethyl-a-naphthylsulfonyloxy groups.

It is to be understood that the present invention also includes a pharmaceutically acceptable salt and an addition salt of the inventive compound, such as a hydrochloride, hydrobromide or trifluoroacetate addition salt, sodium, potassium and magnesium salt.

In an aspect of the present invention, there is provided the inventive preparation method of the oxazolidinone derivative of formula (I) useful for inhibiting blood coagulation factor Xa, by using the intermediate of formula (V) prepared from 1-fluoro-4-nitrobenzene, as illustrated in Reaction Scheme 2:

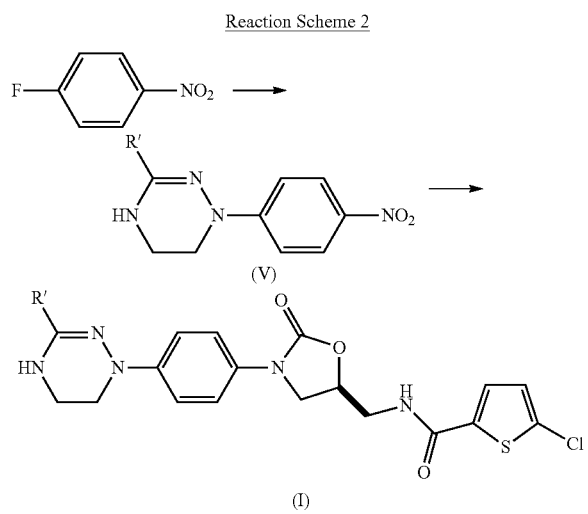

Reaction Scheme 2 wherein, R' has a same meaning as described above.

The compound of formula (I) can be prepared in the form of a salt of various kind, and thus, the present invention also encompasses a salt of the compound of formula (I).

The method for preparing the compound of formula (I) according to the present invention is comprises the following steps of:

subjecting 1-fluoro-4-nitrobenzene to a condensation with 2-hydroxyethylhydrazine in the presence of a base to obtain the compound of formula (II);

treating the compound of formula (II) with an agent having a leaving group X to obtain a compound of formula (III) which has the leaving group X at the position of hydroxyl group in the compound of formula (II);

carrying out a reaction of the compound of formula (III) with a formimidate of formula (IV) to obtain an cyclic amidrazone of formula (V);

introducing an amino protecting group to a cyclic amidrazone of formula (V) to obtain a compound of formula (VI);

reducing the nitro group of the compound of formula (VI) to obtain an aniline of formula (VII);

subjecting the compound of formula (VII) to a reaction with 5-chloro-N-(((S)-oxiran-2-yl)methyl)thiophene-2-carboxamide to obtain a compound of formula (VIII) having a chlorothiophene group;

conducting a carbonylation reaction of the compound of formula (VIII) using a phosgene equivalent to obtain an oxazolidinone of formula (IX); and removing the amino protecting group from the amidrazone ring of the oxazolidinone of formula (IX), as shown in Reaction Scheme 3:

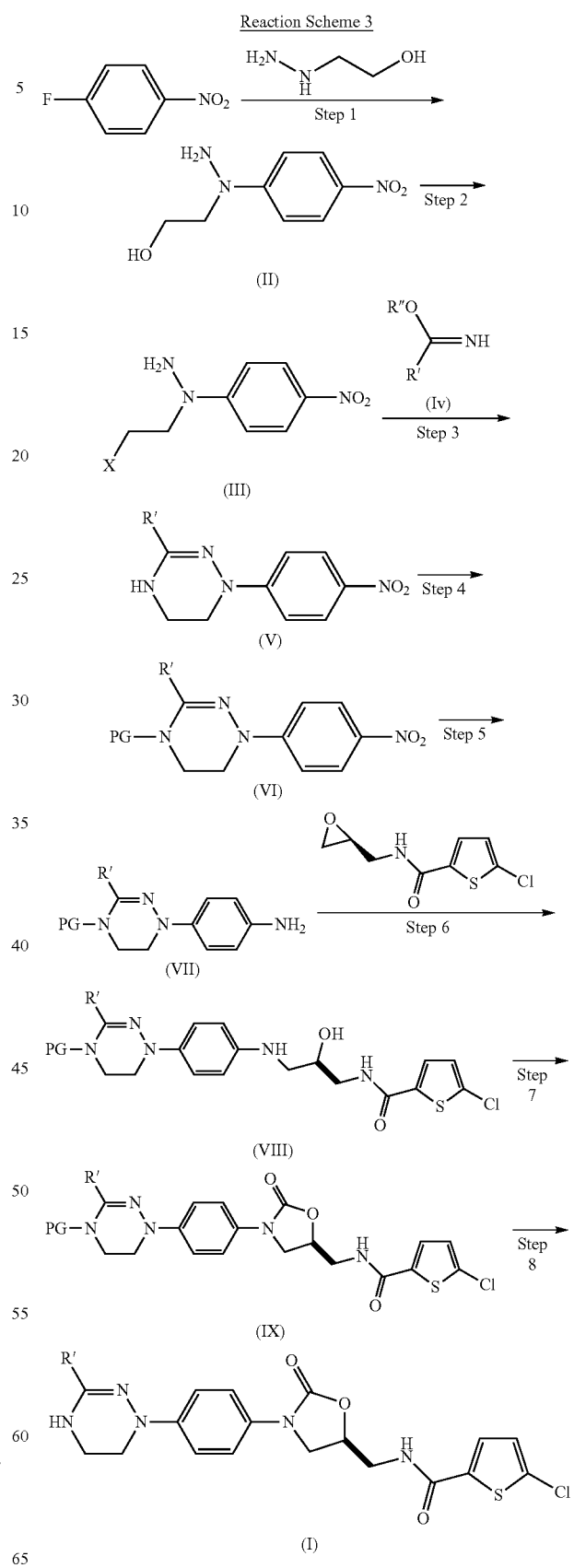

wherein,

X is halogen, ($C_1$-$C_2$ alkyl)sulfonyloxy, substituted ($C_1$-$C_2$ alkyl)sulfonyloxy, ($C_6$-$C_{12}$ aryl)sulfonyloxy, or substituted ($C_6$-$C_{12}$ aryl)sulfonyloxy;

R' is hydrogen, $C_1$-$C_7$ alkyl, $C_3$-$C_7$ cycloalkyl, $C_6$-$C_{12}$ aryl, or $C_4$-$C_{12}$ heteroaryl comprising 1 to 4 hetero atoms selected from the group consisting of oxygen, sulfur, and nitrogen; in which R' may be optionally substituted with one or more substituents selected from the group consisting of $C_1$-$C_7$ alkyl, $C_1$-$C_7$ haloalkyl, $C_1$-$C_7$ alkoxy, and halogen;

R" is $C_1$-$C_7$ alkyl, $C_3$-$C_7$ cycloalkyl, or $C_6$-$C_{12}$ aryl; and

PG is an amino protecting group, and is selected from the group consisting of formyl, ($C_1$-$C_7$ alkyl)carbonyl, ($C_1$-$C_7$ haloalkyl)carbonyl, ($C_6$-$C_{12}$ aryl)carbonyl, ($C_1$-$C_7$ alkoxy)carbonyl, ($C_6$-$C_{12}$ aryl)($C_1$-$C_7$ alkoxy)carbonyl, and trityl, but are not limited thereto. Preferably PG is formyl, acetyl, trifluoroacetyl, methoxycarbonyl, ethoxycarbonyl, t-butyoxycarbonyl, benzyloxycarbonyl, trityl, or benzoyl.

The Reaction scheme 3 is merely illustrative of the preparation methods by which the compounds of the invention may be prepared and are not intended to limit the scope of the invention as defined in the appended claims.

Hereinafter, description of the preparation method illustrated in Reaction Scheme 3 by each step will be given in detail.

<Step 1>

The compound of formula (II) is prepared by conducting a condensation of 1-fluoro-4-nitrobenzene with 2-hydroxyethylhydrazine in the presence of a base.

The condensation is carried out in a solvent at the temperature of 20 to 150° C., preferably at the temperature capable of refluxing solvent, 40 to 100° C., more preferably at 60 to 90° C.

As the solvent, preferred is an inert solvent. Examples of the solvent used in the reaction include, but are not limited to, nitril such as acetonitril; chlorinated hydrocarbon such as dichloromethane or 1,2-dichloroethane; ether such as tetrahydrofuran, diisopropylether, dioxane, or 1,2-dimethoxyethane; aromatic hydrocarbon such as benzene or toluene; amide such as dimethylacetamide or dimethylformamide; and a mixture thereof.

The 2-hydroxyethylhydrazine and base are used in an amount of 1 to 3 mole based on the 1 mole of compound of formula (II) respectively.

There is no specific limitation of the base as long as the reaction is not impeded. Examples of the base include, but are not limited to, carbonates of alkali metals or alkaline earth metals (e.g., sodium carbonate, potassium carbonate, and calcium carbonate); acetates (e.g., sodium acetate and ammonium acetate); hydrogen carbonates of alkali metals (e.g., sodium hydrogen carbonate and potassium hydrogen carbonate); hydroxides of alkali metals (e.g., sodium hydroxide and lithium hydroxide); an organic base (e.g., triethylamine, pyridine, picoline, and tetraethylammonium hydroxide); and a mixture thereof.

Optionally, the reaction may be conducted in a two-phase system using a solvent immiscible with the reactant and water in the presence of a phase transfer catalyst (e.g., tetrabutyl ammonium bromide and benzyl triethylammonium iodide).

In one embodiment of the present invention, the reaction is carried out in acetonitril using potassium carbonate as a base in the presence of 2-hydroxyethylhydrazine (1 to 1.5 equiv.) with reflux. The work-up to isolate and purify the reaction product is carried out by an extract method using a water-immiscible solvent and a precipitation method of amine salts. It is preferable that ethylacetate is used in extracting. The resulting extract is cooled to about 10° C., treated with hydrochloric acid or bromic acid, preferably bromic acid, and filtered simply to obtain hydrochloride or hydrobromide of the compound of formula (II) as a solid <Step 2>

The compound of formula (III) is prepared by treating the compound of formula (II) with an agent having a leaving group X. As a result, the hydroxyl group in the compound of formula (II) is turned to the leaving group X. The leaving group X is halogen, or sulfonyloxy including ($C_1$-$C_2$ alkyl) sulfonyloxy, substituted ($C_1$-$C_2$ alkyl)sulfonyloxy, ($C_6$-$C_{12}$ aryl)sulfonyloxy, and substituted ($C_6$-$C_{12}$ aryl)sulfonyloxy. Examples for the leaving group X include, but are not limited to, chloro, bromo, iodo, methylsulfonyloxy, ethylsulfonyloxy, trifluoromethylsulfonyloxy, phenylsulfonyloxy, p-methylphenylsulfonyloxy, p-bromophenyl sulfonyloxy, and p-nitrophenylsulfonyloxy, preferably bromo.

The changing method of hydroxyl group into the leaving group X has been well known in the relevant art. For example, when the leaving group X is bromo, the alkylbromide of formula (III) or its salt may be prepared by conducting a reaction of the compound of formula (II) or its salt with an agent for bromination. Examples of the agent for bromination include, but are not limited to, phosphorous compound such as phosphorus bromide (e.g., phosphorus tribromide, phosphorus, and pentabromide); and triphenylphosphine dibromide. The reaction is carried out in ether solvent such as tetrahydrofuran, diisopropylether, dioxane, or 1,2-dimethoxyethane at a temperature of −20 to 120° C. There is no specific limitation of the solvent usable in the reaction as long as the reaction is not impeded. The reaction may be conducted in a conventional organic solvent such as methylene chloride, chloroform, or benzene.

In one embodiment of the present invention, the reaction is conducted using 1,2-dimethyoxyethane as a solvent and phosphorous tribromide (1.2 equiv.). The work-up is carried out by a washing method using water which leads to chang of pH, an extract method using a water-immiscible solvent, and a precipitation method of amine salts. In particular, after completion of the reaction, the resulting product is concentrated and the resulting dude bormate of formula (III) is dissolved in water. A base, preferably sodium hydroxide or sodium dicarbonate is added thereto to be pH 2 to 10, preferably pH 4 to 7. The resulting reaction mixture is filterd off to obtain the hydrobromide of formula (III) as a solid. Subsequently, the hydrobromide of formula (III) is neutralized using a conventional method to obtain the compound of formula (III) as a free base.

<Step 3>

The compound of formula (V) is prepared by conducting an amidrazone cyclization of the compound of formula (III).

In particular, the compound of formula (III) is mixed with a solvent and a formimidate of formula (IV) or its hydrochloride salt is added thereto in an amount of 1 to 1.5 mole based on the 1 mole of compound of formula (III) at the temperature of −20 to 30° C., followed by adding a base at the temperature of 20 to 150° C.

Ethylformimidate hydrochloride is used as the formimidate of formula (IV), which is commercially available or can be prepared using a well known preparation method (U.S. Pat. No. 5,948,785).

As the solvent, preferred is an inert solvent. Examples of the solvent used therein include, but are not limited to, nitril such as acetonitril; ester such as ethylacetate; chlorinated hydrocarbon such as dichloromethane or 1,2-dichloroethane; ether such as tetrahydrofuran, diisopropylether, dioxane, or 1,2-dimethoxyethane; aromatic hydrocarbon such as benzene or toluene; amide such as dimethylacetamide or dimethylformamide; and a mixture thereof.

There is no specific limitation of the base as long as the reaction is not impeded. Examples of the base include, but are not limited to, carbonates of alkali metals or alkaline earth metals (e.g., sodium carbonate, potassium carbonate, and calcium carbonate); acetates (e.g., sodium acetate and ammonium acetate); hydrogen carbonates of alkali metals (e.g., sodium hydrogen carbonate and potassium hydrogen carbonate); an organic base (e.g., triethylamine, pyridine, and picoline); and a mixture thereof.

In one embodiment of the present invention, the reaction is carried out by mixing the compound of formula (III) with ethylformimidate hydrochloride (1 to 1.5 equiv.) and sodium acetate (1.5 to 2.5 equiv.) in 1,2-dimethoxyethane. Preferably, the compound of formula (III) is completely dissolved in 1,2-dimethoxyethane and ethylformimidate hydrochloride is added thereto at the temperature of −20 to 30° C., more preferably 10 to 25° C. The resulting suspension is stirred for 5 to 30 min, preferably 10 min and sodium acetate is added thereto, followed by stirring 6 to 50 hrs, preferably 15 hrs with reflux. The work-up is carried out by an extraction method which comprises a process of dissolving the reactant in water in a condition of acidic and uses an organic solvent (e.g., ethylacetate). The aqueous solution thus obtained is treated with a base (e.g., sodium carbonate and sodium hydrogen carbonate) to be pH 8 to 10, preferably 8 to 9 and filtered off to obtain the compound of formula (V) as a solid.

<Step 4>

The compound of formula (VI) is prepared by conducting a pretection reaction of nucleophlic nitrogen of the amidrazone ring of compound of formula (V).

PG is an amino protecting group and examples thereof include, but are not limited to, acyl such as formyl, alkanoyl (e.g., ($C_1$-$C_7$ alkyl)carbonyl such as acetyl; ($C_1$-$C_7$ haloalkyl) carbonyl such as trifluoroacetyl; ($C_1$-$C_7$ alkoxy)carbonyl such as methoxycarbonyl, ethoxycarbonyl, or t-butoxycarbonyl; and ($C_6$-$C_{12}$ aryl)($C_1$-$C_7$ alkoxy)carbonyl such as benzyloxycarbonyl), aroyl such as ($C_6$-$C_{12}$ aryl)carbonyl (e.g., benzoyl), and trityl, preferably t-butoxycarbonyl.

The protection reaction of nucleophlic nitrogen is known well in the organic synthesis field (e.g., L. Paquette, ed. Encyclopedia of Reagents for Organic Synthesis, John Wiley and Sons (1995); T. W. Greene and P. G. M. Wuts, Protective Groups in Organic Synthesis, 2nd ed., John Wiley and Sons, New York, Chapter 7, 1991).

The reaction is carried out at the temperature of 20 to 150° C., preferably at the temperature capable of refluxing solvent 40 to 100° C., more preferably at 60 to 90° C.

As the solvent, preferred is an inert solvent. Examples of the solvent used in the reaction include, but are not limited to, nitril such as acetonitril; ester such as ethylacetate; chlorinated hydrocarbon such as dichloromethane or 1,2-dichloroethane; ether such as tetrahydrofuran, diisopropylether, dioxane, or 1,2-dimethoxyethane; aromatic hydrocarbon such as benzene or toluene; amide such as dimethylacetamide or dimethylformamide; and a mixture thereof.

In one embodiment of the present invention, the reaction is carried out by reacting the compound of formula (V) with di-tert-butylpyrocarbonate ($Boc_2O$, 1 to 2 equiv.) as a protecting reagent, and 4-dimethylaminopyridine (0.03 to 0.07 equiv.) as an activator in tetrahydrofuran for 1 to 5 hrs, preferably 1.5 hrs with reflux. The work-up is carried out by an extraction method which comprises a process of dissolving 4-dimethylaminopyridine in water in a condition of acidic and uses a water-immicisible solvent (e.g., dichloromethanol). The resulting organic layer is concentrated and the solid residue thus obtained is conducted by a trituration using nonpolar organic solvent, preferably cyclohexane, followed by filtering to obtain the compound of formula (VI).

<Step 5>

The aniline of formula (VII) is prepared by reducing the nitro group of the compound of formula (VI) in an inert solvent.

There is no specific limitation of the inert solvent as long as the reaction is not impeded. Examples for the solvent include, but are not limited to, alcohols such as methanol, ethanol or propanol; ether such as tetrahydrofuran, diisopropylether, dioxane, or 1,2-dimethoxyethane; organic acid such as acetic acid; inorganic acid such as hydrochloric acid; water; and a mixture thereof.

The reduction of nitro group is carried out by conducting a stoichiometric hydrogenation using a reductant or metal. Examples of the reductant usable therein include, but are not limited to, a borane complex, diborane, sodium borohydride, lithium borohydride, sodium borohydride-lithium chloride, aluminum lithium hydride, diisobutylaluminum hydride, or zinc chloride. Further, examples of the metal and include, but are not limited to, a transition metal such as zinc, iron, or tin, preferably zinc, which is used in a condition of acidic. Because zinc can be used under neutral or basic conditions, it is preferable to use zinc in the stoichiometric hydrogenation. It is preferable that the stoichiometric hydrogenation is carried out by treating the compound of formula (VI) with zinc in the presence of ammonium chloride. The stoichiometric hydrogenation may be carried out using raney-nickel; palladium on carbon; palladium oxide; platinum; platinum black; platinum oxide; platinum sulfate on carbon; and a transition metal such as rhodium, ruthenium or aluminum under a normal pressure. When the reduction is conducted, it is preferable that ammonium formate, sodium dihydrogene phosphate or hydrazine is used as a hydrogen generater. In a condition of acidic, the reaction is carried out using the reductant in a stoichiometric amount or more, preferably using an excessive amount of the reductant. In the stoichiometric hydrogenation, it is preferable that raney-nickel is used in an amount of 5 to 30% by weight based on the total weight of the compound of formula (VII), and precious metal such as platinum or palladium is used in an amount of 0.02 to 30% by weight based on the total weight of the compound of formula (VII). The reaction is carried out at the temperature of 0 to 150° C., preferably 10 to 100° C. The reaction time depends on the amount of reactant or reaction temperature, preferably a few minutes to 48 hrs.

After completion of the reaction in a condition of acidic, ice water is added to the resulting solution comprising the desired compound and the desired compound is isolated using a basic solvent extract method. Further, after completion of the stoichiometric hydrogenation is used, the compound of formula (VII) is isolated by conducting a filteration of the resulting solution comprising the desired compound to remove the used reductant or metal, and carrying out a concentration the filterate and optionally a recrystallization.

For the solvent in crystallization process, water-miscible solvent is used, and samples thereof include, but are not limited to, $C_1$-$C_4$ alcohol such as methanol, ethanol, n-propanol, isopropanol, n-butanol, or isobutanol; cyclic ether such as tetrahydrofuran or dioxane; amide such as dimethylformamide or N-methylpyrrolidone; acetonitrile; dimethylsulfoxide; a mixture thereof; and a mixture solvent of the above solvent and water.

A seed crystal of the compound of formula (VII) may be used.

Further, a solvent system of water and at least one water-immiscible solvent may be used. Examples of the water-immiscible solvent include, but are not limited to, hydrocarbon such as toluene or xylene; $C_4$-$C_8$ ester such as ethyl acetate; $C_4$-$C_8$ ether such as t-buthylmethylether or isopropyl ether; a chlorinated solvent such as dichloromethane, dichloroethane, or chlorobenzene; and a mixture thereof. When the water-immiscible solvent is used, the compound of formula (VII) is filtered and isolated in an organic phase or aqueous phase. For the solvent in recrystallization process, isopropanol is preferable.

In one embodiment of the present invention, the reaction is carried out by reacting the compound of formula (VI) in the presence of the palladium on carbon, in an alcoholic solvent, preferably methanol, under a hydrogen gas for 1 to 5 hrs, preferably 2 hrs with stirring. In a work-up, the resulting solution is filtered to remove the used reductant or metal and the crude thus obtained is recrystallized to obtain the compound of formula (VII).

<Step 6>

The compound of formula (VIII) is prepared by conducting a nucleophilic displacement reaction of the compound of formula (VII) with 5-chloro-N-(((S)-oxiran-2-yl)methyl)thiophene-2-carboxamide in a solvent.

5-chloro-N-(((S)-oxiran-2-yl)methyl)thiophene-2-carboxamide is commercially available from RStech Corporation in Korea. It is preferable that 5-chloro-N-(((S)-oxiran-2-yl)methyl)thiophene-2-carboxamide is used in an amount of 1 to 2 mole based on the 1 mole of compound of formula (VII). But stoichiometric amount thereof may be used in the reaction.

The solvent used in the reaction is an inert solvent. Examples of the solvent include, but are not limited to, alcohol such as isopropanol or isobutanol; nitril such as acetonitril; ester such as ethylacetate; chlorinated hydrocarbon such as dichloromethane or 1,2-dichloroethane; ether such as tetrahydrofuran, diisopropylether, dioxane, or 1,2-dimethoxyethane; aromatic hydrocarbon such as benzene or toluene; amide such as dimethylacetamide or dimethylformamide; and a mixture thereof.

The reaction is carried out at the temperature of the range comprising the boiling point of the solvent, preferably 20 to 180° C.

In another embodiment of the present invention, the reaction is conducted by stifling the compound of formula (VII) in the presence of 5-chloro-N-(((S)-oxiran-2-yl)methyl)thiophene-2-carboxamide (1 to 1.5 equiv.) in isobutylalcohol for 5 to 30 hrs, preferably 10 to 20 hrs with reflux. In the work-up, the resulting solution is concentrated, and the solid residue is triturated using a non-polar organic solvent, preferably ethylacetae, at the temperature of −10 to 40° C., preferably −5 to 10° C., and filtered to obtain the compound of formula (VIII).

<Step 7>

The oxazolidinone of formula (IX) is prepared by conducting a carbonylation reaction of the vicinal amino alcohol of formula (VIII) using a phosgene equivalent as a condensing agent.

Examples of the condensing agent usable in the reaction include, but are not limited to, ethyl chloroformate, 1,1'-carbonyldiimidazole, and a mixture thereof.

A activator is further used in the reaction, and examples thereof include, but are not limited to, di($C_1$-$C_4$ alkyl)aminopyridine (e.g., 4-dimethylaminopyridine), N-heterocycloalkylpyridine (e.g., 4-pyrrolidinopyridine), and a mixture thereof.

The condensing agent is used in an amount of 1 to 3 mole based on the 1 mole of compound of formula (VIII) and the activator is used in a stoichiometric amount or less based on the compound of formula (VIII). The reaction is carried out at the temperature of 20 to 150° C., preferably at the temperature capable of refluxing solvent, 40 to 100° C., more preferably at 60 to 90° C.

Examples of the solvent used in the reaction include, but are not limited to, nitril such as acetonitril; ester such as ethyl acetate; chlorinated hydrocarbon such as dichloromethane or 1,2-dichloroethane; ether such as tetrahydrofuran, diisopropylether, dioxane, or 1,2-dimethyoxyethane; aromatic hydrocarbon such as benzene or toluene; amide such as dimethylaceamide or dimethylformamide; and a mixture thereof.

In another embodiment of the present invention, the reaction is conducted by reacting the compound of formula (VIII) with 1,1'-carbonyldiimidazol (1 to 1.5 equiv.) in the presence of 4-dimethylaminopyridine (0.03 to 0.06 equiv.) in isobutylalcohol for 1 to 40 hrs, preferably 10 to 25 hrs with reflux. The work-up is carried out by an extraction method which comprises a process of dissolving imidazole and 4-dimethylaminopyridine in water in a condition of acidic, and uses a water-immicisible solvent, e.g., ethylacetate. More preferably, the resulting mixture is stirred until a completion of the reaction with reflux to crystallize the compound of formula (IX), cooled to a temperature of 10 to 60° C., preferably 30° C., and filtered to obtain the compound of formula (IX).

Alternatively, the compound of formula (IX) may be crystallized by adding a seed crystal of the compound of formula (IX) to the resulting mixture after 1 to 5 hrs of the reaction.

<Step 8>

5-Chloro-N-({(5S)-2-oxo-3-[4-(5,6-dihydro-4H-[1,2,4]triazin-1-yl)phenyl]-1,3-oxazolidin-5-yl}-methyl)thiophene-2-carboxamide of formula (I) is prepared by removing the amino protecting group from the compound of formula (IX). The deprotection of the amino protecting group is carried out depending on the kind of the protecting group. For example, an acyl or aroyl group in the compound of formula (IX) is removed by conducting a hydrolysis using an alkali metal hydroxide such as lithium hydroxide or sodium hydroxide. Alternatively, the acyl group such as t-butoxycarbonyl is removed using an acid such as hydrochloric acid, sulfuric acid, trifluoroacetic acid, or an acidic cation exchange resin. And the arylalkoxycarbonyl group such as benzyloxycarbonyl is removed by conducting a hydrogenation using a catalyst such as a palladium on carbon, or by conducting a reaction with a Lewis acid such as boron tris (trifluoroacetate). The deprotection method of the amino protecting group has been known in a organic synthesis field (T. W. Greene and P. G. M. Wuts, Protective Groups in Organic Synthesis, 2nd ed., John Wiley and Sons, New York, Chapter 7, 1991).

When PG is t-butoxycarbonyl in the compound of formula (IX), the deprotection is carried out using 1 to 6 N of hydrochloric acid, preferably 3 N of hydrochloric acid in ether solution such as tetrahydrofuran, diisopropylether, dioxane, or 1,2-dimethoxyethan, preferably tetrahydrofuran at the temperature of 20 to 150° C., preferably at the temperature capable of refluxing solvent, 40 to 100° C., more preferably at 60 to 90° C. for 0.5 to 3 hrs, preferably 1 hr, with reflux.

There is no specific limitation of the solvent usable in the reaction as long as the reaction is not impeded. Examples of the solvent include, but are not limited to, methylene chloride, chloroform, benzene, and tetrahydrofuran.

The work-up is carried out by an extraction method which comprises a process of converting the oxazolidinone hydrochloride of formula (I) having a cyclic amidrazone group into the derivative of formula (I) as a free salt, and uses a water-immicisible solvent, e.g., ethylacetate. More preferably, the resulting mixture is stirred until a completion of the reaction with reflux to crystallize the derivative of formula (I), cooled to a temperature of 10 to 70° C., preferably 30° C., and filtered to obtain the compound of formula (I). Alternatively, the derivative of formula (I) may be crystallized by adding a seed crystal of the derivative of formula (I) to the resulting mixture after 0.5 to 1 hr of the reaction.

It is to be understood that the present invention also includes a pharmaceutically acceptable salt of the inventive compound, which salt prepared by treating a pharmaceutically acceptable free acid. The free acid comprises an inorganic acid such as hydrochloric acid, bromic acid, sulfuric acid, or phosphoric acid; and an organic acid such as citric acid, acetic acid, lactic acid, maleic acid, fumaric acid, gluconic acid, methylsulfonic acid, succinic acid, 4-toluenesulfonic acid, trifluoroacetic acid, galacturonic acid, embonic acid, glutamine, or aspartic acid.

The present invention also includes all hydrates of the salt of formula (I). In particular, when the salt has a hygroscopic property, it is preferable that the salt is used in the form of crystalline hydrates.

The solvent and the agent used in the present invention may be replaced with functional substitutes or derivatives which are known in the related field, the reaction time and temperature are controlled properly to optimize the reaction conditions. Further, the present invention further comprises an isolating process of the resulting product from the reaction, and optionally a conventional purification process such as extraction, crystallization, and trituration.

The 5-chloro-N-({(5S)-2-oxo-3-[(5,6-dihydro-4H-[1,2,4]triazin-1-yl)phenyl]-1,3-oxazolidin-5-yl}-methyl)-2-thiophene carboxamide of the present invention is a inhibitor of blood coagulation factor, which is useful for treating or preventing thrombosis, myocardial infarction, arteriosclerosis, inflammation, stroke, angina pectoris, recurrent stricture after angioplasty, or thromboembolism such as intermittent claudication.

In accordance with the method of the present invention using the cyclic amidrazone of formula (V) as an intermediate, a high-purity 5-chloro-N-({(5S)-2-oxo-3-[4-(5,6-dihydro-4H-[1,2,4]triazin-1-yl)phenyl]-1,3-oxazolidin-5-yl}-methyl)thiophene-2-carboxamide can be prepared economically in a high yield. Further, the preparation method of the present invention is suitable for a mass production because the preparation method comprises crystallization and extracting process capable of mass production for isolating and refining.

The present invention is further described and illustrated in Examples provided below, which are, however, not intended to limit the scope of the present invention.

Preparation Example 1

Preparation of Ethyl Formimidate Hydrochloride

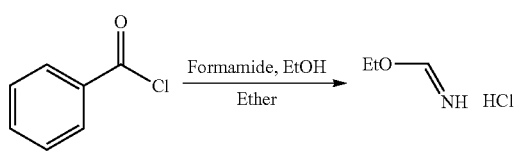

To a solution of benzoyl chloride (1212 g, 8.62 mol, 1 eq) in anhydrous ether (5.8 L) was added dropwise a solution of formamide (388 g, 8.62 mol, 1 eq) in EtOH (396 g, 8.60 mol, 0.998 eq) at 0° C. for 1 hr. The mixture thus obtained was stirred at 0° C. for 30 min. The solid was filtered off, washed with ether (3 L) and EA (3 L). The solid was dried under high vacuum.

Yield: 625 g (66%)

Example 1

5-chloro-N-({5S)-2-oxo-3-[(5,6-dihydro-1H-[1,2,4]-triazin-4-yl)phenyl]-1,3-oxazolidin-5-yl}-methyl)-2-thiophene carboxamide hydrochloride Step 1: Preparation of 2-[N-(4-nitro-phenyl)-hydrazino]-ethanol

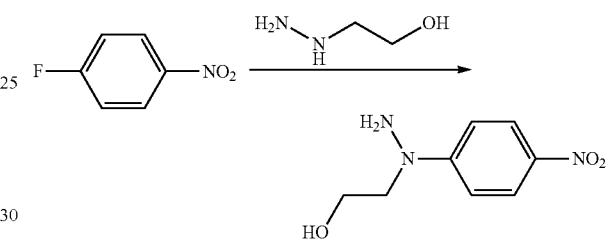

1-Fluoro-4-nitrobenzene (7.1 g, 50 mmol) was dissolved in $CH_3CN$ (70 ml), 2-hydroxyethylhyrazine (purity: 90%, Aldrich, 5.0 g, 66 mmol) and $K_2CO_3$ (7.6 g, 55 mmol) were added thereto. The suspension thus obtained was stirred for 4 hrs with reflux. The resulting orange-colored suspension was concentrated under reduced pressure (reflux condenser, 10 torr, 40° C.) and ethylacetate (EA, 90 ml) and water (18 ml) were added thereto. The resulting mixture was stirred strongly at r.t. for 10 min. The organic layer was extracted and washed with the saturated brine (10 ml). The resulting solution was cooled to 10° C. and 48% HBr solution (3.7 ml) was added thereto dropwise with stirring. The pale yellow colored solid thus obtained was filtered off and dried under high vacuum (1 torr, 40° C.) to obtain the title compound as an intermediate.

Yield: 7.1 g (51%).

TLC: $R_f$=0.62 (EA/MeOH/AcOH=20/1/0.5)

$^1$H NMR (600 MHz, DMSO-$d_6$) δ 8.17 (d, J=9.0 Hz, 2H), 7.12 (d, J=9.0 Hz, 2H), 3.82 (t, J=5.4 Hz, 2H), 3.69 (t, J=5.4 Hz, 2H)

LCMS: 198 (M+H$^+$) ($C_8H_{11}N_3O_3$)

Step 2: Preparation of 1-bromo-2-[N-(4-nitro-phenyl)-hydrazino]-ethane

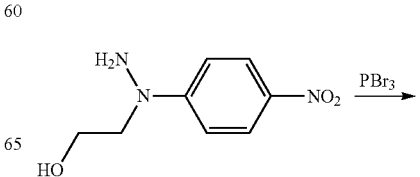

-continued

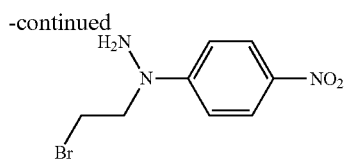

The compound obtained in Step 1 (38.9 g, 0.140 mol) was suspended in anhydrous 1,2-dimethoxyethane (585 ml). The resultant suspension was cooled to 0° C. and PBr₃ (15.9 ml, 0.168 mol) was added thereto dropwise for 30 min. The mixture thus obtained was stirred at 60° C. for 4 hrs. The pale yellow colored solution thus obtained was concentrated under reduced pressure (reflux condenser, 10 torr, 45° C.). The resultant residue (oil) was suspended with water (150 ml) and stirred. Aq. sat'd NaHCO₃ solution (150 m) was added to the resultant suspension to be pH 4. The resulting mixture was stirred for 30 min to precipitate the pale yellow colored precipitates. The precipitates were filtered off and washed with water (100 ml). The resulting solid was mixed with water (100 ml), aq. sat'd NaHCO₃ solution (70 ml) and CH₂Cl₂ (500 ml). The resulting mixture was stirred for 10 min and stood to separate organic and aqueous layers. The organic layer was dried over 20 g of MgSO₄ and filtered off. The resulting filtrate was concentrated under reduced pressure (reflux condenser, 10 torr, 40° C.) to obtain the title compound as a pale yellow solid.

Yield: 31.3 g (86%)
TLC: $R_f$=0.91 (EA/MeOH/AcOH=20/1/0.5)
$^1$H NMR (600 MHz, CDCl₃) δ 8.14 (d, J=10.2 Hz, 2H), 6.92 (d, J=10.2 Hz, 2H), 4.00 (t, J=7.2 Hz, 2H), 3.65 (t, J=7.2 Hz, 2H)
LCMS: 261 (M+H⁺) (C₈H₁₀BrN₃O₂)

Step 3: Preparation of 4-(5,6-dihydro-4H-[1,2,4]triazin-1-yl)-1-nitrobenzene

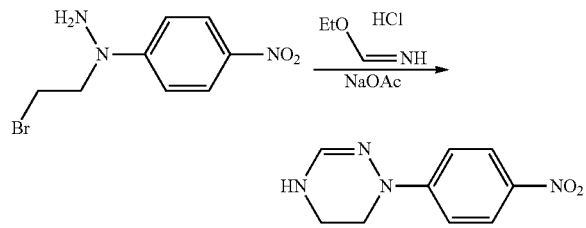

The compound obtained in Step 2 (13.0 g, 50.0 mmol) was completely dissolved in anhydrous 1,2-dimethoxyethane (200 ml) which is prepared by mixing 1,2-dimethoxyethane (purity: 99%, Junsei Co. Ltd) with an desired amount of molecular sieve 4A and standing for 5 hrs or more with stirring at times. Ethyl formimidate HCl salt (5.8 g, 52.5 mmol) was added thereto. The suspension thus obtained was stirred at 25° C. for 10 min. Anhydrous sodium acetate (NaOAc, 8.6 g, 105 mmol) was added thereto and stirred for 15 hrs with reflux. The orange colored suspension thus obtained was concentrated under reduced pressure (10 torr, 50° C.). The orange colored residue thus obtained was mixed with 1N HCl (140 ml), EA (50 ml) and hexane (100 ml), and stirred at r.t for 10 min. A small amount of insoluble suspended solids was remained in aqueous layer and filtered off. The resulting aqueous layer was washed with a mixture of EA (30 ml) and hexane (60 ml). 12 g of sodium carbonate was added to the resulting solution to be pH 8.5. The orange colored solid thus obtained was filtered off under reduced pressure, washed with water (15 ml) and dried under vacuum to obtain the title compound.

Yield: 7.7 g (75%).
TLC: $R_f$=0.45 (EA/MeOH/AcOH=20/1/0.5)
HPLC: $R_t$=8.65 (Gradient A), purity 91.1%
$^1$H NMR (400 MHz, DMSO-d₆) δ 8.03 (d, J=9.6 Hz, 2H), 7.16 (d, J=9.6 Hz, 2H), 7.12 (br s, 1H), 7.01 (d, J=4.0 Hz, 2H), 3.77 (t, J=5.2 Hz, 2H), 3.43-3.40 (m, 2H)
LCMS: 207 (M+H⁺) (C₉H₁₀N₄O₂)

Step 4: Preparation of 4-(5,6-dihydro-4-t-butoxycarbonyl-[1,2,4]-triazin-1-yl)-1-nitrobenzene

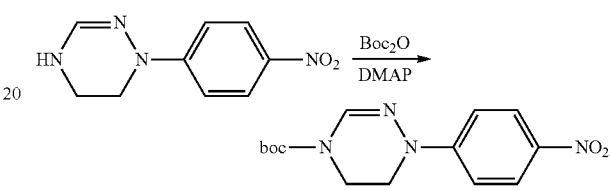

To the orange colored suspension prepared by suspending the compound obtained in Step 3 (12.4 g, 60 mmol) in tetrahydrofurane (THF, 200 ml), 4-dimethylaminopyridine (DMAP, 0.367 g, 3 mmol) and di-tert-butyl dicarbonate (Boc₂O, 19.6 g, 90 mmol) were added and stirred with reflux for 1.5 hrs. The yellow colored suspension thus obtained was concentrated under reduced pressure (reflux condenser, 10 torr, 40) to remove the solvent. The resulting yellow colored residue was completely dissolved in CH₂Cl₂ (700 ml) and washed with 1N HCl (700 ml). The organic layer was extracted, dried over 25 g of MgSO₄, and concentrated under reduced pressure (condenser, 10 torr, 40). The resultant yellow colored residue was dissolved in cyclohexane (250 ml) and stirred strongly at r.t. for 30 min. The resulting mixture was concentrated under reduced pressure to obtain yellow colored solids. The solids were dried (1 torr, 50) to obtain a disried compound.

Yield: 15.6 g (85%)
TLC: $R_f$=0.93 (EA/MeOH/AcOH=20/1/0.5)
$^1$H NMR (600 MHz, DMSO-d₆) δ 8.14 (d, J=9.6 Hz, 2H), 7.62 (br s, 1H), 7.30 (d, J=9.6 Hz, 2H), 3.89 (br s, 2H), 3.79 (br s, 2H), 1.50 (s, 9H)
LCMS: 307 (M+H⁺) (C₁₄H₁₈N₄O₄)

Step 5: Preparation of 4-(5,6-dihydro-4-t-butoxycarbonyl-[1,2,4]-triazin-1-yl)aniline

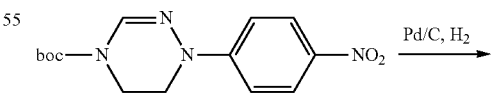

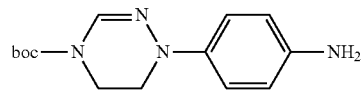

To the yellow colored suspension prepared by suspending the compound obtained in Step 4 (19.9 g, 65 mmol) in methanol (200 ml), 10% palladium on carbon (4.0 g) was added. The resulting mixture was subjected to vacuum outgassing and stirred at r.t., for 2 hrs in the flask connected with hydrogen bollum. The resulting mixture was filtered through celite 545 under redued pressure to remove the palladium on carbon. The filtrate was concentrated under reduced pressure (reflux condenser, 10 torr, 40). The resulting pale brown colored residue was dissolved in isopropylalcohol (140 ml) and refluxed to dissolve completely. The resulting solution was stood at 0 for 2 hrs to cool, stirred for 30 min and filtered off under redued pressure. The resulting ivory crystalline solid was dried in vacuo to obtain the title compound (15.8 g, 88%).

TLC: $R_f$=0.38 (EA/MeOH/AcOH=20/1/0.5)

$^1$H NMR (400 MHz, DMSO-$d_6$) δ 7.34 (br s, 1H), 6.91 (d, J=12.0 Hz, 2H), 6.51 (d, J=12.0 Hz, 2H), 6.64 (br s, 2H), 3.74 (br s, 2H), 3.41 (br s, 2H), 1.48 (s, 9H)

LCMS: 277 (M+H$^+$) ($C_{14}H_{20}N_4O_2$)

colored solution thus obtained was concentrated under reduced pressure (reflux condenser, 10 torr, 50). To the yellow solid residue thus obtained, ethylacetate (200 ml) was added and the resulting mixture was stirred at r.t. for 30 min and further stirred strongly at 0 for 30 min. The suspended solid thus obtained was filtered off under reduced pressure and dried in vacuum (1 torr, 50) to obtain the title compound as ivory crude.

Yield: 25.9 g (75%)

TLC: $R_f$=0.34 (EA/MeOH/AcOH=20/1/0.5)

$^1$H NMR of a crude sample (600 MHz, DMSO-$d_6$) δ 8.62 (t, J=5.4 Hz, 1H), 7.69 (d, J=3.6 Hz, 1H), 7.36 (br s, 1H), 7.18 (d, J=4.2 Hz, 1H), 6.95 (d, J=9.0 Hz, 2H), 6.54 (d, J=9.0 Hz, 2H), 5.10 (t, J=6.6 Hz, 1H), 5.05 (d, J=5.4 Hz, 1H), 3.81-3.75 (m, 3H), 3.44 (br s, 2H), 3.37-3.34 (m, 1H), 3.25-3.21 (m, 1H), 3.08-3.04 (m, 1H), 2.94-2.89 (m, 1H), 1.48 (s, 9H)

LCMS: 494 (M+H$^+$) ($C_{22}H_{28}ClN_5O_4S$)

Step 7: Preparation of 5-chloro-N-({(5S)-2-oxo-3-[(5,6-dihydro-4-t-butoxycarbonyl-[1,2,4]-triazin-1-yl)phenyl]-1,3-oxazolidin-5-yl}-methyl)-2-thiophene carboxamide

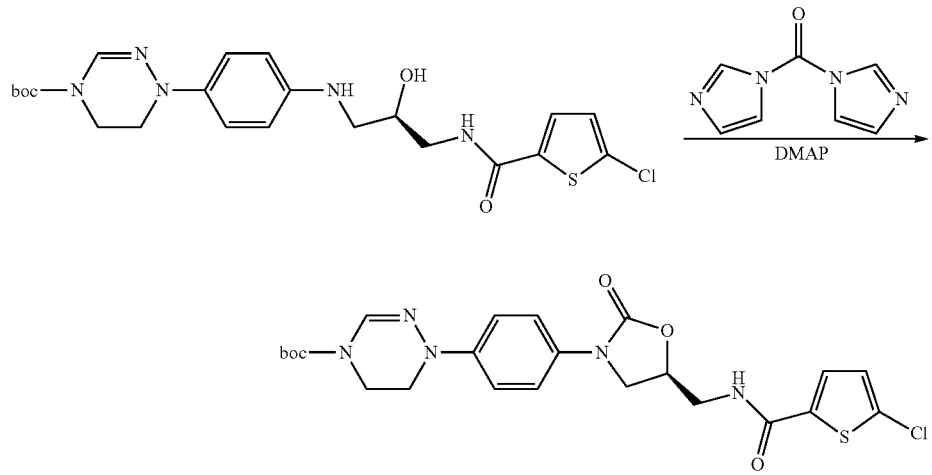

Step 6: Preparation of N-(3-(5,6-dihydro-4-t-butoxycarbonyl-[1,2,4]-triazin-1-yl)anilino-(2R)-2-hydroxypropyl)-5-chloro-2-thiophene carboxamide

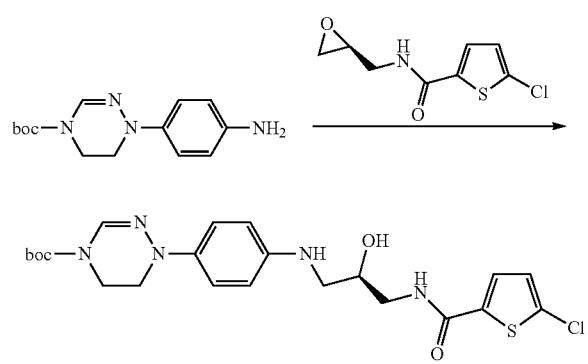

The compound obtained in Step 5 (19.3 g, 70 mmol) and 5-chloro-N-(((S)-oxiran-2-yl)methyl)thiophene-2-carboxamide (19.1 g, 88 mmol) were suspended in isobutyl alcohol (350 ml) and stirred for 18 hrs with reflux. The dark blue The compound obtained in Step 6 (25.2 g, 51 mmol) was completely dissolved in THF (325 ml), and 1.1'-carbonyldiimidazole (10.8 g, 66 mmol) and DMAP (0.31 mg, 2.6 mmol) were added thereto. The resulting mixture was stirred with reflux for 18 hrs. The resulting pale yellow colored suspension was cooled to r.t, concentrated under reduced pressure and dried in vacuo (1 torr, 50) to obtain the title compound as an ivory solid.

Yield: 23.3 g (88%)

TLC: $R_f$=0.75 (EA/MeOH/AcOH=20/1/0.5)

$^1$H NMR (400 MHz, DMSO-$d_6$) δ 8.97 (t, J=5.4 Hz, 1H), 7.69 (d, J=4.2 Hz, 1H), 7.43 (br s, 1H), 7.41 (d, J=9.0 Hz, 2H), 7.20 (d, J=4.2 Hz, 1H), 7.19 (d, J=9.0 Hz, 2H), 4.82-4.77 (m, 1H), 4.12 (t, J=9.0 Hz, 1H), 3.80-3.78 (m, 3H), 3.62 (br s, 2H), 3.59 (t, J=6.0 Hz, 2H), 1.49 (s, 9H)

LCMS: 520 (M+H$^+$) ($C_{23}H_{26}ClN_5O_5S$)

Step 8: Preparation of 5-chloro-N-({(5S)-2-oxo-3-[(5,6-dihydro-4H-[1,2,4]-triazin-1-yl)phenyl]-1,3-oxazolidin-5-yl}-methyl)-2-thiophene carboxamide hydrochloride

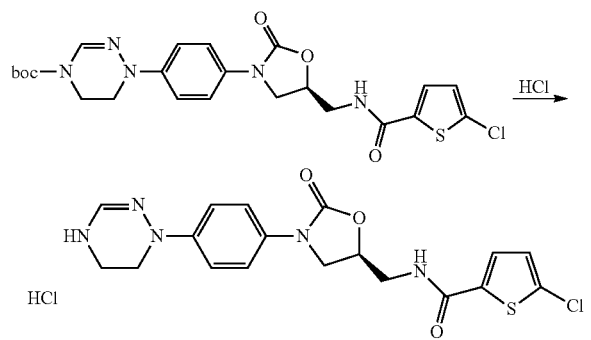

The compound obtained in Step 7 (16.1 g, 31 mmol) was completely dissolved in THF (193 ml), 3N HCl (193 ml) was added thereto. The resulting solution was stirred with reflux for 1 hr. The white suspension thus obtained was cooled to r.t., concentrated under reduced pressure and dried in vacuo (1 torr, 40) to obtain the title compound as a white solid.

Yield: 13.4 g (95%)
TLC: $R_f$=0.82 (MC/MeOH/AcOH=10/1/0.5)
HPLC: $R_t$=12.39 (Gradient A), purity 99.5%
$^1$H NMR (600 MHz, DMSO-d$_6$) δ 12.12 (br s, 1H), 10.20 (br s, 1H), 9.08 (t, J=6.0 Hz, 1H), 8.60 (d, J=5.2 Hz, 1H), 7.74 (d, J=4.2 Hz, 1H), 7.53 (d, J=9.0 Hz, 2H), 7.20 (d, J=4.2 Hz, 1H), 7.13 (d, J=9.0 Hz, 2H), 4.85-4.81 (m, 1H), 4.15 (t, J=8.8 Hz, 1H), 3.85 (dd, J=6.0, 9.2 Hz, 1H), 3.66 (t, J=4.8 Hz, 2H), 3.63-3.56 (m, 2H), 3.19 (br s, 2H)
LCMS: 420 (M+H$^+$) (C$_{18}$H$_{18}$ClN$_5$O$_3$S)

Example 2

Preparation of 5-chloro-N-({(5S)-2-oxo-3-[(5,6-dihydro-4H-[1,2,4]-triazin-1-yl)phenyl]-1,3-oxazolidin-5-yl}-methyl)-2-thiophene carboxamide

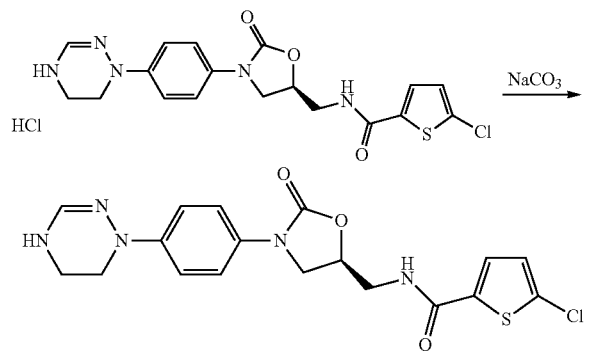

The HCl salt obtained in Example 1 (6.9 g, 15 mmol) was completely dissolved in 33% methanol aqueous solution (1.1 L) and heated to 50 while stirring. To the resulting colorlessness solution, 0.6M aq. Na$_2$CO$_3$ solution (25 ml) was added and the white suspension thus obtained was stood at 0 for 0.5 hr to cool. The white solid thus obtained was concentrated under reduced pressure, wished with H$_2$O (150 ml) and dried in vacuo (1 torr, 40) to obtain the title compound (yield: 5.5 g, 87%). The title compound was dissolved in methanol (330 ml) and stirred with reflux. The pale yellow colored solution thus obtained was stood at 0 for 2 hrs to cool. The resulting white solid was concentrated under reduced pressure, washed with methanol (10 ml), and dried in vacuo (1 torr, 40) to obtain a crystal of the title compound (yield: 5.0 g, 80%).

HPLC: $R_t$=12.37 (Gradient A), purity 99.7%
$^1$H NMR (400 MHz, DMSO-d$_6$) δ 8.97 (t, J=6.0 Hz, 1H), 7.69 (d, J=4.0 Hz, 1H), 7.32 (d, J=9.2 Hz, 2H), 7.20 (d, J=4.0 Hz, 1H), 7.12 (d, J=9.2 Hz, 2H), 6.79 (d, J=4.0 Hz, 1H), 6.52 (br s, 1H), 4.80-4.75 (m, 1H), 4.10 (t, J=8.8 Hz, 1H), 3.77 (dd, J=6.0, 9.2 Hz, 1H), 3.58 (t, J=5.6 Hz, 2H), 3.33 (s, 4H)
LCMS: 420 (M+H$^+$) (C$_{18}$H$_{18}$ClN$_5$O$_3$S)

Example 3

Preparation of 5-chloro-N-({(5S)-2-oxo-3-[(5,6-dihydro-4H-[1,2,4]-triazin-1-yl)phenyl]-1,3-oxazolidin-5-yl}-methyl)-2-thiophene carboxamide methane sulfonate

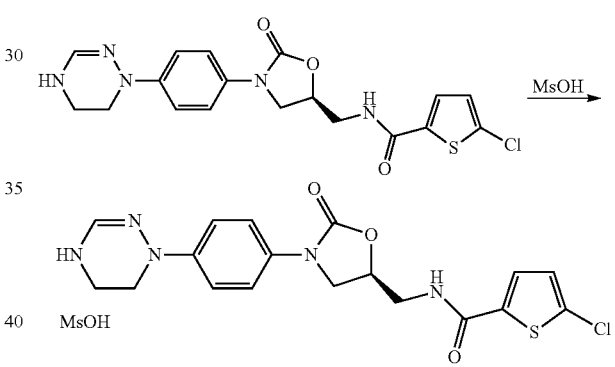

To the compound obtained in Example 2 (3.3 g, 7.9 mmol), a mixture solution of MeOH/CH$_2$Cl$_2$ (1/4 v/v, 70 ml) was added and stirred with reflux. The pale yellow colored solution thus obtained was cooled to 0 and methylsulfonic acid (0.56 ml, 8.6 mmol) was added thereto. The resulting mixture was concentrated under reduced pressure (reflux condenser, 10 torr, 40) to obtain pale yellow foamy solid. To the resultant solid, absolute ethanol (20 ml) was added and the resulting mixture was stirred with reflux to dissolve solid clearly. The resulting solution was cooled to 0 to 2 hrs. The resulting white solid was concentrated under reduced pressure, washed with absolute EtOH (5 ml), and dried in vacuo (1 torr, 40) to obtain a crystalline methane sulfonate.

Yield: 3.8 g (93%)
HPLC: $R_t$=12.35 (Gradient A), purity 99.8%
$^1$H NMR (400 MHz, DMSO-d$_6$) δ 11.97 (br s, 1H), 10.07 (br s, 1H), 8.99 (t, J=6.0 Hz, 1H), 8.59 (d, J=6.0 Hz, 1H), 7.70 (d, J=4.0 Hz, 1H), 7.53 (d, J=9.2 Hz, 2H), 7.20 (d, J=4.0 Hz, 1H), 7.13 (d, J=9.2 Hz, 2H), 4.86-4.80 (m, 1H), 4.16 (t, J=9.2 Hz, 1H), 3.82 (dd, J=6.0, 9.2 Hz, 1H), 3.67 (m, 2H), 3.60 (t, J=5.6 Hz, 2H), 3.20 (br s, 2H), 2.31 (s, 3H)
LCMS: 420 (M$^+$H$^+$)(C$_{18}$H$_{18}$ClN$_5$O$_3$S)

Example 4

(S)-5-chloro-N-((3-(4-(5,6-dihydro-1,2,4-triazin-1 (4H)-yl)phenyl)-2-oxooxazolidin-5-yl)methyl) thiophene-2-carboxamide methane sulfonate Step 1: Preparation of (2-[N-(4-nitro-phenyl)-hydrazinyl]-ethanol) hydrobromide

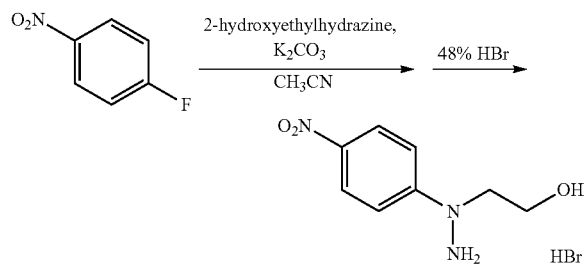

1-Fluoro-4-nitrobenzene (428 g, 3.03 mol, Aldrich F11204) was dissolved in CH$_3$CN (4.3 L), and 2-hydroxyethylhyrazine (300 g, 3.94 mol, 1.3 eq, imported from China, >98%) and K$_2$CO$_3$ (461 g, 3.34 mol, 1.1 eq, Aldrich 347825) were added thereto. The mixture thus obtained was stirred at 80 for 19 hrs. The mixture was cooled to r.t. and evaporated to remove solvent. The residue was dissolved with EA (1.5 L) and H$_2$O (1 L). The organic layer was extracted and washed with H$_2$O (500 mL) and brine (200 mL). The extracted EA layer was cooled to 0 and 48% HBr solution (360 mL, Aldrich 244260) was added thereto dropwise at 0 with stirring. The resultant mixture was stirred at 0 for 1 hr. The solid thus obtained was filtered off and washed with EA (5 L). The obtained solid was dried under high vacuum to obtain the title compound.

Yield: 531 g (63%)
TLC: R$_f$=0.62 (EA/MeOH/AcOH=20/1/0.5)
$^1$H NMR (400 MHz, DMSO-d$_6$) δ 7.94 (d, J=9.6 Hz, 2H), 7.12 (br s, 2H), 6.63 (d, J=9.2 Hz, 2H), 3.53 (t, J=5.8 Hz, 2H), 3.19 (t, J=5.8 Hz, 2H)
LCMS: 198 (M+H$^+$) (C$_8$H$_{11}$N$_3$O$_3$)

Step 2: Preparation of 1-bromo-2-[N-(4-nitro-phenyl)-hydrazino]-ethane

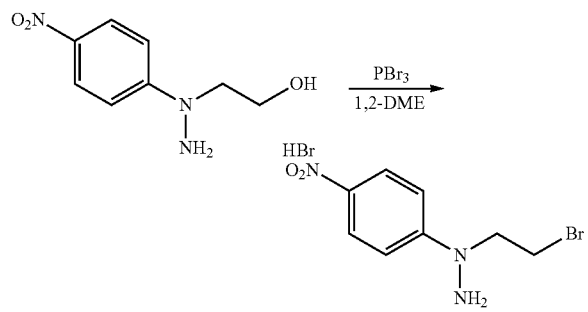

The compound obtained in Step 1 (531 g, 1.90 mol) was suspended in anhydrous 1,2-dimethoxyethane (4.5 L). The resultant suspension was cooled to and PBr$_3$ (220 mL, 2.29 mol, 1.2 eq, Aldrich 256536) was added thereto dropwise at 0. The mixture thus obtained was warmed up to r.t. and stirred at 60 for 15 hrs.

The mixture was cooled to r.t., and filtered off to remove remained insoluble solid. The filter cake thus obtained was washed with 1,2-dimethoxyethane (700 mL) and the filtrate was concentrated in vacuo. The resultant residue was suspended with H$_2$O (2.5 L), stirred and cooled to 0. Aq. 2N NaOH solution (1.7 L) was added thereto at 0 to neutralize the suspension mixture (pH 6-7). The solid was filtered off and washed with H$_2$O (5 L). The filtered solid was air-dried for 5 hrs.

The air-dried solid was dissolved with CH$_2$Cl$_2$ (3 L), and aq. sat'd NaHCO$_3$ solution (1.5 L) and H$_2$O (700 mL) were added thereto. The resultant mixture was stirred for 15 min and stood to separate organic and aqueous layers. Insoluble solid which was not dissolved in organic layer and H$_2$O was remained in the mixture. The mixture was filtered off to remove insoluble solid and the filter cake was washed with CH$_2$Cl$_2$ (700 mL). The organic layer was extracted, dried over MgSO$_4$, filtered off, and concentrated in vacuo. The resultant solid was dried under high vacuum to obtain the title compound.

Yield: 383 g (77%: When product was dissolved in CDCl$_3$ to check the $^1$H NMR spectroscopy, insoluble solid was stilled remained in CDCl$_3$)
TLC: R$_f$=0.91 (EA/MeOH/AcOH=20/1/0.5)
$^1$H NMR (400 MHz, CDCl$_3$) δ 8.12 (d, J=9.6 Hz, 2H), 6.92 (d, J=9.2 Hz, 2H), 4.00 (t, J=6.6 Hz, 2H), 3.65 (t, J=6.6 Hz, 2H)
LCMS: 261 (M+H$^+$) (C$_8$H$_{10}$BrN$_3$O$_2$)

Step 3: Preparation of 4-(5,6-dihydro-4H-[1,2,4]-triazin-1-yl)-1-nitrobenzene

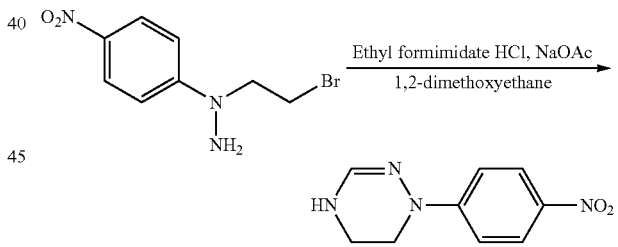

The compound obtained in Step 2 (384 g, 1.48 mol) was dissolved in anhydrous 1,2-dimethoxyethane (4 L) and ethyl formimidate HCl salt (322 g, 2.94 mol, 2 eq) was added thereto at r.t. The resultant mixture was stirred at r.t. for 30 min. NaOAc (364 g, 4.44 mol, 3.0 eq, Aldrich 110191) was added to the mixture and the mixture was stirred at 75 for 15 hrs.

The mixture was cooled to r.t. and evaporated to remove solvent. The resultant residue was suspended in EA (2 L) and 1,2-dimethoxyethane (1 L). Aq. 3N HCl solution (2.5 L) was added to the suspension. Insoluble solid was remained in resultant mixture. The solid was filtered off two times to remove insoluble solid. Ether (3 L) was added to the filtrate to separate organic and aqueous layers effectively. Aqueous layer was separated and washed with mixed organic solution (EA (1 L)+Hexane (500 mL)). The combined organic layer should be kept to recover the product.

(The Treatment of Aqueous Layer)

The aqueous layer was cooled to 0 and aq. 6N NaOH solution (2.2 L) was added thereto slowly to basify the H$_2$O layer (pH~9). The resultant suspension was stirred at r.t. for 12 hrs. The solid was filtered off and washed with H$_2$O (3 L) and dried under high vacuum.

(The Treatment of Combined Organic Layer)

The combined organic layer was concentrated in vacuo. The resultant residue was acidified with aq. 3N HCl solution (500 mL). Filtration was carried out to remove insoluble solid. The filtrate (H$_2$O layer) thus obtained was washed with ether (700 mL×2). The aqueous layer was stirred and cooled to 0. Aq. 5N NaOH solution (1 L) was added to the cooled aqueous layer to basify (pH~9). The mixture thus obtained was stirred at r.t. for 12 hrs. The solid thus obtained was filtered off and washed with H$_2$O (1.5 L). The solid was dried under high vacuum to obtain the title compound.

Yield: 187 g (62%)

TLC: R$_f$=0.45 (EA/MeOH/AcOH=20/1/0.5)

$^1$H NMR (400 MHz, DMSO-d$_6$) δ 7.99 (d, J=9.6 Hz, 2H), 7.16 (d, J=9.6 Hz, 2H), 7.09 (br s, 1H), 6.97 (d, J=3.6 Hz, 2H), 3.73 (t, J=5.0 Hz, 2H), 3.45-3.46 (m, 2H)

LCMS: 207 (M+H$^+$) (C$_9$H$_{10}$N$_4$O$_2$)

Step 4: Preparation of 4-(5,6-dihydro-4-t-butoxycarbonyl-[1,2,4]-triazin-1-yl)-1-nitrobenzene

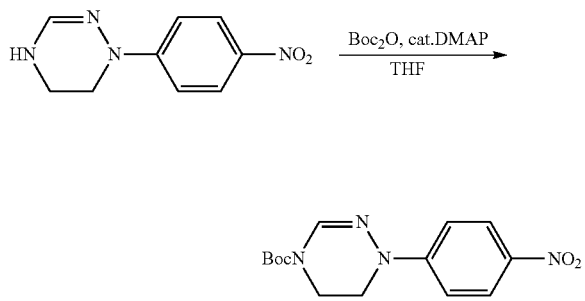

The compound obtained in Step 3 (187 g, 0.907 mol) was suspended in anhydrous THF (2.2 L), and Boc$_2$O (300 g, 1.36 mol, 1.5 eq, Aldrich 205249) and DMAP (6 g, 0.045 mol, 0.05 eq, Aldrich 107700) were added thereto. The mixture thus obtained was stirred at 65 for 5 hrs.

The mixture was cooled to 0. MeOH (1.5 L) was added to the mixture at 0 and stirred at 0 for 1 hr. The solid thus obtained was filtered off, washed with MeOH (750 mL) and dried under high vacuum.

Filtrate thus obtained was concentrated in vacuo. MeOH (1 L) was added to the resultant residue with stirring. The mixture thus obtained was stirred at r.t for 12 hrs. Solid thus obtained was filtered off, washed with MeOH (500 mL), and dried under high vacuum to obtain the title compound.

Yield: 182 g (65%)

TLC: R$_f$=0.93 (EA/MeOH/AcOH=20/1/0.5)

$^1$H NMR (400 MHz, DMSO-d$_6$) δ 8.17 (d, J=9.6 Hz, 2H), 7.57 (br s, 1H), 7.19 (d, J=9.6 Hz, 2H), 3.93-3.86 (m, 2H), 3.83-3.745 (m, 2H), 1.56 (s, 9H)

LCMS: 307 (M+H$^+$) (C$_{14}$H$_{18}$N$_4$O$_4$)

Step 5: Preparation of 4-(5,6-dihydro-4-t-butoxycarbonyl-[1,2,4]-triazin-1-yl)aniline

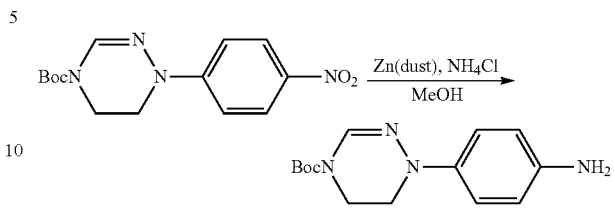

The compound obtained in Step 4 (134 g, 438 mmol) was suspended in MeOH (1.3 L) at r.t., and NH$_4$Cl (12 g, 0.5 eq, Aldrich A4514) and Zn (15 g, 0.5 eq, Aldrich 209988) were added 6 times at intervals of 15 min at r.t. (total amounts of NH$_4$Cl=73 g (1356 mmol, 3.1 eq) and total amounts of Zn=88 g (1356 mmol, 3.1 eq))

Temperature of the resultant mixture was risen gradually to 65 and the mixture was stirred at 65 for 12 hrs. The mixture was cooled to 40 and NH$_4$Cl (12 g, 0.5 eq, Aldrich A4514) and Zn (15 g, 0.5 eq, Aldrich 209988) were added thereto. Temperature of the resultant mixture was risen gradually to 65 and the mixture was stirred at 65 for 1 hr.

The mixture was cooled to r.t. and filtered off through celite pad. The filter cake was washed with MeOH (700 mL) and THF (700 mL) and the filtrate was concentrated. The crude product thus obtained was dried under high vacuum and used without further purification.

Yield: 124 g (quantitative)

TLC: R$_f$=0.38 (EA/MeOH/AcOH=20/1/0.5)

$^1$H NMR (400 MHz, DMSO-d$_6$) δ 7.31 (br s, 1H), 6.86 (d, J=12.0 Hz, 2H), 6.48 (d, J=12.0 Hz, 2H), 4.60 (s, 2H), 3.71 (br s, 2H), 3.38 (br s, 2H), 1.44 (s, 9H)

LCMS: 277 (M+H$^+$) (C$_{14}$H$_{20}$N$_4$O$_2$)

Step 6: Preparation of N-(3-(5,6-dihydro-4-t-butoxycarbonyl-[1,2,4]-triazin-1-yl)anilino-(2R)-2-hydroxypropyl)-5-chloro-2-thiophene carboxamide

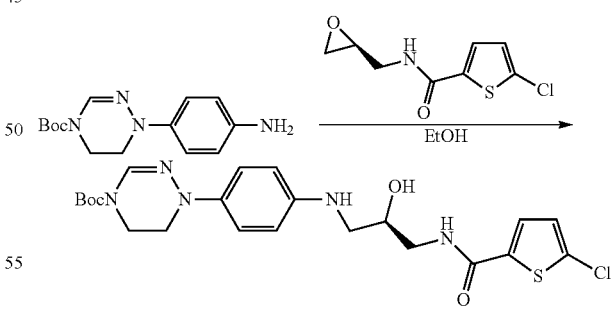

The compound obtained in Step 5 (120 g, 435 mmol) and 5-chloro-N-(((S)-oxiran-2-yl)methyl)thiophene-2-carboxamide (123 g, 566 mmol, 1.3 eq, purchased from RStech (Daejeon, Korea) was suspended in absolute EtOH (1450 mL). The mixture thus obtained was stirred at 85 for 16 hrs. The mixture was cooled to r.t. and evaporated in vacuo to remove solvent. The resultant residue was dried under high vacuum for 18 hrs. The dried solid was suspended in EA (2 L). The suspension thus obtained was stirred at r.t. for 1 hr. The solid thus obtained was filtered off and washed with EA (500 mL) and ether (500 mL). The filtered solid was dried under high vacuum to obtain the title compound.

Aniline (starting material), epoxide, over-reacted by product were contained in crude product.

Yield: 158 g (74%)

TLC: $R_f$=0.34 (EA/MeOH/AcOH=20/1/0.5)

$^1$H NMR of a crude sample (400 MHz, DMSO-$d_6$) δ 8.57 (t, J=5.4 Hz, 1H), 7.65 (d, J=3.6 Hz, 1H), 7.32 (br s, 1H), 7.14 (d, J=4.2 Hz, 1H), 6.90 (d, J=9.0 Hz, 2H), 6.51 (d, J=9.0 Hz, 2H), 5.04 (t, J=6.6 Hz, 1H), 5.00 (d, J=5.4 Hz, 1H), 3.87-3.65 (m, 3H), 3.40 (br s, 2H), 3.37-3.34 (m, 1H), 3.25-3.21 (m, 1H), 3.17-2.96 (m, 1H), 2.94-2.84 (m, 1H), 1.44 (s, 9H)

LCMS: 494 (M+H$^+$) ($C_{22}H_{28}ClN_5O_4S$)

Step 7: Preparation of 5-chloro-N-({(5S)-2-oxo-3-[(5,6-dihydro-4-t-butoxycarbonyl-[1,2,4]-triazin-1-yl)phenyl]-1,3-oxazolidin-5-yl}-methyl)-2-thiophene carboxamide

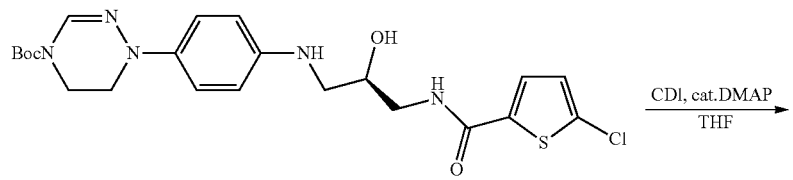

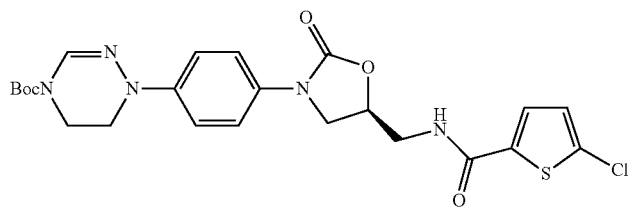

The compound obtained in Step 6 (158 g, 320 mmol) was suspended in THF (1000 mL), and 1,1-carbonyldiimidazole (68 g, 416 mmol, 1.3 eq, Aldrich 115533) and DMAP (2 g, 16 mmol, 0.05 eq, Aldrich 107700) were added thereto. The mixture thus obtained was stirred at 75 for 3 hrs, cooled to r.t., and evaporated in vacuo to remove solvent. The resultant residue was suspended in EtOH (1300 mL). The suspension thus obtained was stirred at 0 for 1 hr. The solid thus produced was filtered off and washed with cold EtOH (800 mL) and cold MeOH (300 mL). The filtered solid was dried under high vacuum to obtain the title compound.

Yield: 101 g (61%)

TLC: $R_f$=0.75 (EA/MeOH/AcOH=20/1/0.5)

$^1$H NMR (400 MHz, DMSO-$d_6$) δ 8.93 (t, J=5.4 Hz, 1H), 7.66 (d, J=4.2 Hz, 1H), 7.43-7.33 (m, 3H), 7.29-7.12 (m, 3H), 4.82-4.73 (m, 1H), 4.09 (t, J=9.0 Hz, 1H), 3.82-3.70 (m, 3H), 3.65-3.52 (m, 4H), 1.45 (s, 9H)

LCMS: 520 (M+H$^+$) ($C_{23}H_{26}ClN_5O_5S$)

Step 8: Preparation of 5-chloro-N-({(5S)-2-oxo-3-[(5,6-dihydro-4H-[1,2,4]-triazin-1-yl)phenyl]-1,3-oxazolidin-5-yl}-methyl)-2-thiophene carboxamide hydrochloride

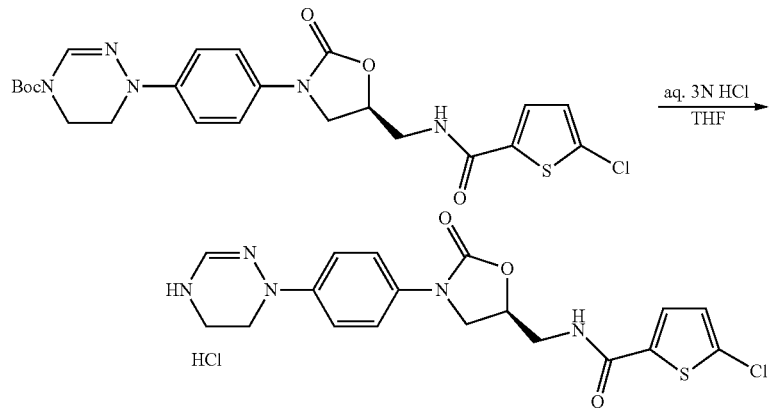

The compound obtained in Step 7 (101 g, 194 mmol) was suspended in aq. 3N HCl solution (1.1 L) and THF (1.1 L), and stirred at 80 for 3 hrs. The mixture thus obtained was cooled to r.t. The solid thus produced was filtered off, washed with THF (700 mL) and dried under high vacuum to obtain the title compound.

Yield: 75 g (85%)
TLC: $R_f$=0.82 (MC/MeOH/AcOH=10/1/0.5)
$^1$H NMR (400 MHz, DMSO-$d_6$) δ 12.12 (br s, 1H), 10.32 (br s, 1H), 9.13 (t, J=6.0 Hz, 1H), 8.57 (d, J=5.2 Hz, 1H), 7.75 (d, J=4.2 Hz, 1H), 7.49 (d, J=9.0 Hz, 2H), 7.15 (d, J=4.2 Hz, 1H), 7.09 (d, J=9.0 Hz, 2H), 4.85-4.74 (m, 1H), 4.11 (t, J=8.8 Hz, 1H), 3.85 (dd, J=6.0, 9.2 Hz, 1H), 3.62 (t, J=4.8 Hz, 2H), 3.59-3.49 (m, 2H), 3.15 (br s, 2H)
LCMS: 420 (M+H$^+$) (C$_{18}$H$_{18}$ClN$_5$O$_3$)

Example 5

Preparation of 5-chloro-N-({(5S)-2-oxo-3-[(5,6-dihydro-4H-[1,2,4]-triazin-1-yl)phenyl]-1,3-oxazolidin-5-yl}-methyl)-2-thiophene carboxamide

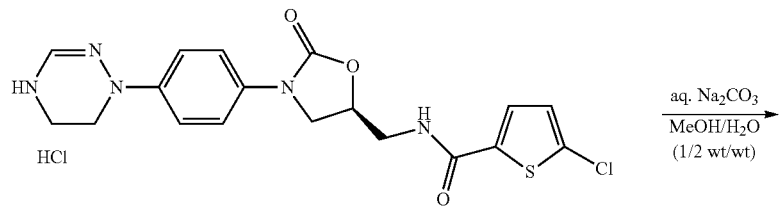

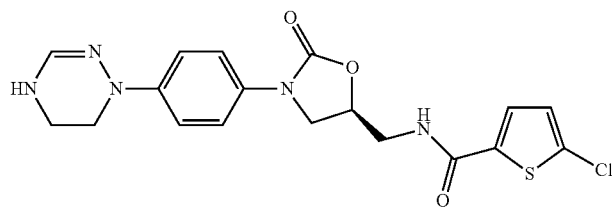

The compound obtained in Example 4 (20 g, 43.8 mmol) was suspended in MeOH/H$_2$O (1/2 wt/wt, 3.2 L) and stirred at 100 until the compound obtained in Example 4 was dissolved clearly. 0.6M aq. Na$_2$CO$_3$ solution (75 mL) was added thereto. The mixture thus obtained was stood at 0 for 2 hrs. The solid thus produced was filtered off, washed with H$_2$O (400 mL) and dried under high vacuum to obtain the title compound.

Yield: 17 g (93%)

$^1$H NMR (400 MHz, DMSO-d$_6$) δ 8.93 (t, J=6.0 Hz, 1H), 7.66 (d, J=4.0 Hz, 1H), 7.29 (d, J=9.2 Hz, 2H), 7.16 (d, J=4.0 Hz, 1H), 7.08 (d, J=9.2 Hz, 2H), 6.76 (d, J=4.0 Hz, 1H), 6.48 (br s, 1H), 4.78-4.69 (m, 1H), 4.07 (t, J=8.8 Hz, 1H), 3.74 (dd, J=6.0, 9.2 Hz, 1H), 3.54 (t, J=5.6 Hz, 2H), 3.38 (s, 4H)

LCMS: 420 (M+H$^+$) (C$_{18}$H$_{18}$ClN$_5$O$_3$)

Example 6

Preparation of 5-chloro-N-({(5S)-2-oxo-3-[(5,6-dihydro-4H-[1,2,4]-triazin-1-yl)phenyl]-1,3-oxazolidin-5-yl}-methyl)-2-thiophene carboxamide methane sulfonate

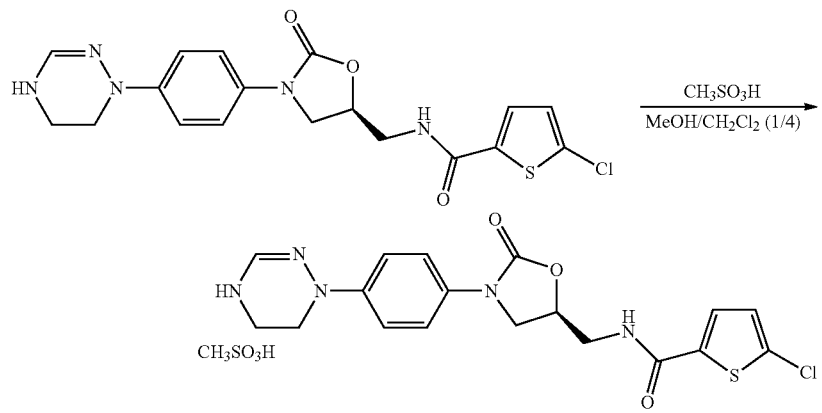

The compound obtained in Example 5 (16.7 g, 39.8 mmol) was suspended in MeOH/CH$_2$Cl$_2$ (1/4 v/v, 350 mL) and stirred at 50 until the compound obtained in Example 5 was dissolved clearly. The mixture thus obtained was cooled to 0 and methylsulfonic acid (2.9 mL, 43.8 mmol, 1.3 eq, Aldrich 471356) was added thereto at 0. The resulting mixture was evaporated in vacuo to remove solvent. The resultant solid was suspended in absolute EtOH (100 mL) and the suspension was stirred at 90 to dissolve solid clearly. The resulting mixture was cooled to 0 and stirred at 0 for 2 hrs. The solid thus produced was filtered off, washed with absolute EtOH (100 mL), and dried under high vacuum to obtain the title compound.

Yield: 18.4 g (89.7%)

$^1$H NMR (400 MHz, DMSO-d$_6$) δ 11.93 (br s, 1H), 10.03 (br s, 1H), 8.94 (t, J=6.0 Hz, 1H), 8.55 (d, J=6.0 Hz, 1H), 7.66 (d, J=4.0 Hz, 1H), 7.49 (d, J=9.2 Hz, 2H), 7.16 (d, J=4.0 Hz, 1H), 7.08 (d, J=9.2 Hz, 2H), 4.93-4.87 (m, 1H), 4.10 (t, J=9.2 Hz, 1H), 3.77 (dd, J=6.0, 9.2 Hz, 1H), 3.63 (m, 2H), 3.57 (t, J=5.6 Hz, 2H), 3.16 (br s, 2H), 2.28 (s, 3H)

LCMS: 420 (M+H$^+$) (C$_{18}$H$_{18}$ClN$_5$O$_3$)

While the invention has been described with respect to the above specific embodiments, it should be recognized that various modifications and changes may be made to the invention by those skilled in the art which also fall within the scope of the invention as defined by the appended claims.

What is claimed is:

1. A method for preparing an oxazolidinone derivative of formula (I) or a pharmaceutically acceptable salt thereof, comprising the steps of:

introducing an amino protecting group to a cyclic amidrazone of formula (V) to obtain a compound of formula (VI);

reducing the nitro group of the compound of formula (VI) to obtain a compound of formula (VII);

subjecting the compound of formula (VII) to a reaction with 5-chloro-N-(((S)-oxiran-2-yl)methyl)thiophene-2-carboxamide to obtain a compound of formula (VIII) having a chlorothiophene group;

conducting a carbonylation reaction of the compound of formula (VIII) using a phosgene equivalent to obtain an oxazolidinone of formula (IX); and removing the amino protecting group from the amidrazone ring of the oxazolidinone of formula (IX),

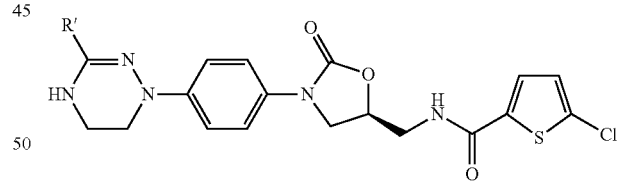

(I)

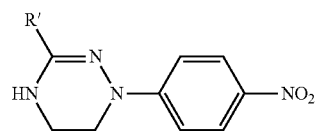

(V)

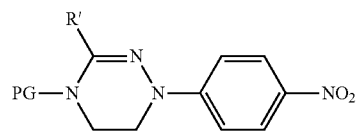

(VI)

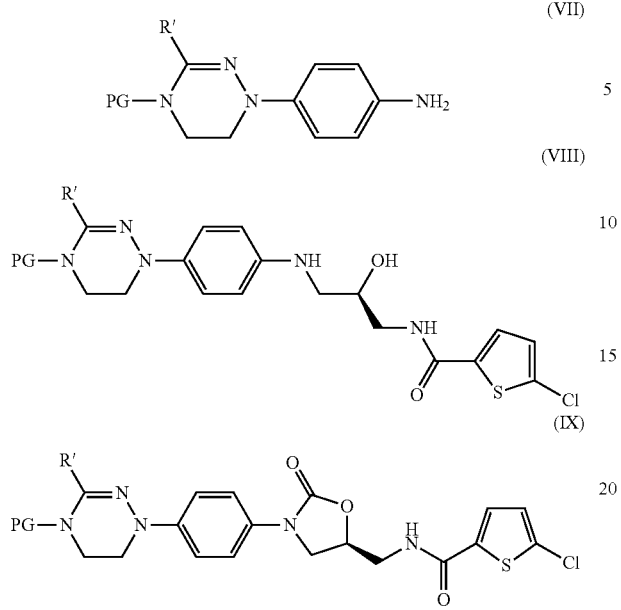

wherein,

R' is hydrogen, $C_1$-$C_7$ alkyl, $C_3$-$C_7$ cycloalkyl, or $C_4$-$C_{12}$ heteroaryl comprising 1 to 4 hetero atoms selected from the group consisting of oxygen, sulfur, and nitrogen; in which R' may be optionally substituted with one or more substituents selected from the group consisting of $C_1$-$C_7$ alkyl, $C_1$-$C_7$ haloalkyl, $C_1$-$C_7$ alkoxy, and halogen; and PG is formyl, ($C_1$-$C_7$ alkyl)carbonyl, ($C_1$-$C_7$ haloalkyl)carbonyl, ($C_6$-$C_{12}$ aryl)carbonyl, ($C_1$-$C_7$ alkoxy)carbonyl, ($C_6$-$C_{12}$ aryl)($C_1$-$C_7$ alkoxy)carbonyl, or trityl.

2. The method according to claim 1, wherein the phosgene equivalent is ethyl chloroformate or 1,1'-carbonyldiimidazole.

3. The method according to claim 1, wherein the cyclic amidrazone of formula (V) is prepared by a method comprising the steps of:

subjecting 1-fluoro-4-nitrobenzene to a condensation with 2-hydroxyethylhydrazine in the presence of a base to obtain the compound of formula (II);

treating the compound of formula (II) with an agent having a leaving group X to obtain a compound of formula (III); and carrying out a reaction of the compound of formula (III) with a formimidate of formula (IV),

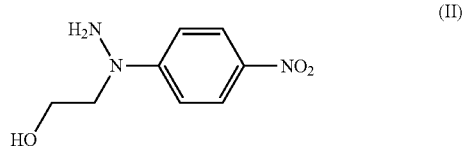

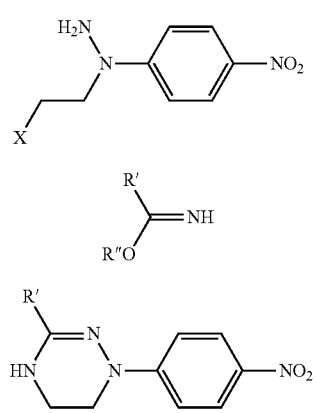

wherein,

X is halogen, ($C_1$-$C_2$ alkyl)sulfonyloxy, substituted ($C_1$-$C_2$ alkyl)sulfonyloxy, ($C_6$-$C_{12}$ aryl)sulfonyloxy, or substituted ($C_6$-$C_{12}$ aryl)sulfonyloxy;

R' is hydrogen, $C_1$-$C_7$ alkyl, $C_3$-$C_7$ cycloalkyl, or $C_4$-$C_{12}$ heteroaryl comprising 1 to 4 hetero atoms selected from the group consisting of oxygen, sulfur, and nitrogen; in which R' may be optionally substituted with one or more substituents selected from the group consisting of $C_1$-$C_7$ alkyl, $C_1$-$C_7$ haloalkyl, $C_1$-$C_7$ alkoxy, and halogen; and R" is $C_1$-$C_7$ alkyl, $C_3$-$C_7$ cycloalkyl, or $C_6$-$C_{12}$ aryl.

4. The method according to claim 1, wherein the reduction of the nitro group is carried out by stoichiometric hydrogenation using a reductant or metal.

5. The method according to claim 4, wherein the reduction of the nitro group is carried out by treating the compound of formula (VI) with zinc in the presence of ammonium chloride.

6. A cyclic amidrazone of formula (V):

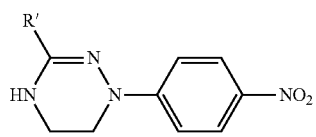

wherein,

R' is hydrogen, $C_1$-$C_7$ alkyl, $C_3$-$C_7$ cycloalkyl, or $C_4$-$C_{12}$ heteroaryl comprising 1 to 4 hetero atoms selected from the group consisting of oxygen, sulfur, and nitrogen; in which R' may be optionally substituted with one or more substituents selected from the group consisting of $C_1$-$C_7$ alkyl, $C_1$-$C_7$ haloalkyl, $C_1$-$C_7$ alkoxy, and halogen.

* * * * *